US012655485B2

(12) United States Patent
Johnson et al.

(10) Patent No.: US 12,655,485 B2
(45) Date of Patent: Jun. 16, 2026

(54) METHOD FOR DIRECT MICROBIAL IDENTIFICATION

(71) Applicant: Quest Diagnostics Investments LLC, Secaucus, NJ (US)

(72) Inventors: Erik P. Johnson, Oceanside, CA (US); Nik Isely, Moraga, CA (US); Jamie L. Platt, San Juan Capistrano, CA (US); Martin Siaw, Irvine, CA (US); Ron M. Kagen, Rancho Santa Margarita, CA (US); Dale A. Schwab, Carlsbad, CA (US)

(73) Assignee: Quest Diagnostics Investments LLC, Secaucus, NJ (US)

( * ) Notice: Subject to any disclaimer, the term of this patent is extended or adjusted under 35 U.S.C. 154(b) by 369 days.

(21) Appl. No.: 17/892,819

(22) Filed: Aug. 22, 2022

(65) Prior Publication Data

US 2023/0143248 A1 May 11, 2023

Related U.S. Application Data

(62) Division of application No. 15/315,877, filed as application No. PCT/US2015/034202 on Jun. 4, 2015, now Pat. No. 11,421,285.

(60) Provisional application No. 62/007,663, filed on Jun. 4, 2014.

(51) Int. Cl.

| | |
|---|---|
| *C12Q 1/68* | (2018.01) |
| *C12Q 1/686* | (2018.01) |
| *C12Q 1/6869* | (2018.01) |
| *C12Q 1/689* | (2018.01) |
| *C12Q 1/6895* | (2018.01) |
| *G16B 30/00* | (2019.01) |

(52) U.S. Cl.
CPC ............. *C12Q 1/689* (2013.01); *C12Q 1/686* (2013.01); *C12Q 1/6869* (2013.01); *C12Q 1/6895* (2013.01); *G16B 30/00* (2019.02); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,251,606 | B1 | 6/2001 | Hseu et al. |
| 2009/0068641 | A1* | 3/2009 | Bergeron ................ A61P 31/04 |
| | | | 435/6.1 |
| 2010/0273219 | A1 | 10/2010 | May et al. |
| 2013/0012399 | A1 | 1/2013 | Myers et al. |
| 2014/0141993 | A1 | 5/2014 | Isshiki et al. |

OTHER PUBLICATIONS

Kim et al; Journal of Clinical Microbiology, vol. 42, pp. 1308-1312; 2004.*
Drancourt et al; Journal of Clinical Microbiology, vol. 40, pp. 1333-1338, 2002.*
Park et al; Microbiology and Immunity, vol. 57, pp. 583-588, 2013.*
Mahenthiralingam et al; Journal of Clinical Microbiology, vol. 38, pp. 3165-3173, 2000.*
Cupakova et al; Acta Vet. BRNO, 2005, vol. 74, pp. 633-637.*
Lee et al; Journal of Applied Microbiology, vol. 111, pp. 893-903, 2011.*
Esfahani et al., "Rapid and accurate identification of *Mycobacterium tuberculosis* complex and common non-tuberculous mycobacteria by multiplex real-time PCR targeting different housekeeping genes," Curr. Microbiol., vol. 65, No. 5, pp. 493-499, Jul. 2014.
International Search Report issued on Nov. 27, 2015 in application No. PCT/US2015/34202.
Meyer et al., "Parallel tagged sequencing on the 454 platform," Nat. Protoc., vol. 3, No. 2, pp. 267-276, Feb. 2008.

* cited by examiner

*Primary Examiner* — Jehanne S Sitton
(74) *Attorney, Agent, or Firm* — DUANE MORRIS LLP

(57) ABSTRACT

Described herein are methods for direct detection of microbial agent(s) in a polymicrobial sample, such as a biological sample from a human, without culturing the microbial agent(s). The direct detection can identify mixtures of bacteria and/or fungi in the sample. Also described are primer sequences and amplification techniques for performing the direct detection methods.

6 Claims, 4 Drawing Sheets

Specification includes a Sequence Listing.

METHOD FOR DIRECT MICROBIAL IDENTIFICATION

CROSS-REFERENCE TO RELATED APPLICATIONS

This application is a Divisional of U.S. application Ser. No. 15/315,877, which is the U.S. National Stage of PCT/US2015/034202, filed Jun. 4, 2015, which claims the benefit of U.S. provisional application No. 62/007,663, filed Jun. 4, 2014, the contents of which are incorporated herein by reference in their entirety.

The instant application contains a Sequence Listing which has been submitted in XML format via Patent Center and is hereby incorporated by reference in its entirety. Said XML copy, created on Dec. 6, 2022, is named 034827-1869.xml and is 446,493 bytes.

FIELD OF THE INVENTION

Methods for direct detection of microbial agent(s) in a sample, including a mixture of bacterial and fungal microbial agents, are disclosed. Nucleotide sequences and amplification techniques to identify microbial agent(s) in a sample also are described.

BACKGROUND OF THE INVENTION

The following description of the background of the invention is provided simply as an aid in understanding the invention and is not admitted to describe or constitute prior art to the invention.

Microbial agents are currently identified by first culturing the agents using media and growth conditions, and then analyzing morphological/biochemical characteristics or DNA sequencing to determine their identity. Culturing isolates the microbial agents so they can be characterized by phenotypic or genotypic methods, and also provides conditions favorable to grow the microbial agents to produce enough material for analysis.

However, culturing has drawbacks. For example, culturing microbial agents is time consuming and not practical in situations where many different agents are presented in a sample. Moreover, recovering microbial agents from culture can be difficult if the culture conditions are not optimized, proper growth conditions are unknown, or certain agents are overgrown and mask the presence of slow-growing agents. The masking of some microbial agents can prevent correctly identifying all microbial agents in a sample.

The masking of some microbial agents is especially problematic with a biofilm sample (e.g., from a chronic wound, a catheter site infection, or due to periodontal disease) because multiple microbial agents can comprise the biofilm, but the most pathogenic specie(s) may be present in the lowest abundance. As a result, a patient's microbial infections are often treated with antibiotics that are not effective in treating their particular infection because the particular pathogenic species is unknown.

A technique to quickly identify all microbial agents in a sample would allow for quicker and more accurate identification of the source(s) of a microbial infection.

SUMMARY OF THE INVENTION

Provided herein are methods for determining the presence or absence of a microbial agent in a sample, comprising (a) contacting a sample containing sample nucleic acids with an amplification reaction mixture, wherein the amplification reaction mixture primers that specifically amplify at least one target sequence of bacterial 16S rDNA, at least one target sequence of fungal ITS rDNA, and at least one target sequence selected each of *Mycobacterium* rpoB, *Staphylococcus* rpoB, *Streptococcus* rpoB, *Burkholderia* recA, *Enterococcus* tuf and *Pseudomonas* gvrB, the generate amplification reaction mixture containing the sample nucleic acids; (b) subjecting the amplification reaction mixture containing the sample nucleic acids to polymerase chain reaction (PCR) conditions to generate microbial amplicons; (c) producing adapter-tagged amplicons by attaching the microbial amplicons of step (b), if present, to nucleic acid adapters; (d) amplifying the adapter-tagged amplicons, if present, from step (c) to generate adapter-tagged amplicons; and (e) sequencing the adapter-tagged amplicons, if present, from step (c), wherein a microbial agent is determined to be present in the sample if a microbial amplicon is present and the sequence of the non-adapter portion of an adapter tagged microbial amplicon is at least 90% identical to a nucleotide fragment of bacterial 16S rDNA or fungal ITS rDNA. In some embodiments, the method further comprises identifying the species of bacteria and/or fungus in the sample as *Mycobacterium, Staphylococcus, Streptococcus, Burkholderia, Enterococcus* and/or *Pseudomonas* gvrB. In some embodiments, the reagent mixture further comprises a DNA polymerase and a plurality of free nucleotides comprising adenine, thymine, cytosine and guanine. In some embodiments, the PCR involves (i) heating the reaction mixture to a first predetermined temperature for a first predetermined time to separate the strands of the double stranded DNA from each other, (ii) cooling the reaction mixture to a second predetermined temperature for a second predetermined time under conditions to allow the first and second primers to hybridize with their complementary sequences on the first and second strands of the target DNA, and to allow Taq polymerase to extend the primers, and (iii) repeating steps (i) and (ii) at least 12 times to amplify microbial nucleic acids, if present, in the sample to produce microbial amplicons.

In some embodiments, BLAST (Basic Local Alignment Search Tool) is performed to make a broad identification based on the universal rDNA sequence followed by a BLAST of the taxon specific genes to provide resolution to species level.

In some embodiments, a post-extraction step is performed on the sample nucleic acids to remove human DNA prior to combining with the amplification reaction mixture.

In some embodiments, the amplification reaction mixture comprises primers comprising any of SEQ ID NOs 1-335. In some embodiments, multiple different target regions are amplified in a multiplexed reaction. In some embodiments, each target sequence amplification is performed in a separate, individual PCR reaction.

In some embodiments, primers that specifically amplify at least one target sequence of bacterial 16S rDNA comprise a sequence selected from among SEQ ID NOs 89-103.

In some embodiments, primers that specifically amplify at least one target sequence of fungal ITS rDNA comprise a sequence selected from among SEQ ID NOs 119-128.

In some embodiments, primers that specifically amplify at least one target sequence of *Mycobacterium* rpoB comprise a sequence selected from among SEQ ID NOs 139-152.

In some embodiments, primers that specifically amplify at least one target sequence of *Streptococcus* rpoB comprise a sequence selected from among SEQ ID NOs 181-233.

In some embodiments, primers that specifically amplify at least one target sequence of *Staphylococcus* rpoB comprise a sequence selected from among SEQ ID NOs 273-298.

In some embodiments, primers that specifically amplify at least one target sequence of *Burkholderia* recA comprise a sequence selected from among SEQ ID NOs 299-306.

In some embodiments, primers that specifically amplify at least one target sequence of *Enterococcus* tuf comprise a sequence selected from among SEQ ID NOs 307-312.

In some embodiments, primers that specifically amplify at least one target sequence of *Pseudomonas* gvrB comprise a sequence selected from among SEQ ID NOs 313-320.

In some embodiments, the primers further comprise a tag sequence selected from the group consisting of SEQ ID NO:3 and SEQ ID NO:4.

In some embodiments, the adapter sequence is selected from the group consisting of SEQ ID NO:1 and SEQ ID NO:2.

In some embodiments, the adapters are attached via a primer comprising the adaptor sequence. In some embodiments, the primer comprising the adaptor sequence further comprises a multiplex identifier sequence. In some embodiments, the primer comprising the adaptor sequence further comprises a tag sequence specific for the microbial amplicon. In some embodiments, the tag sequence is selected from the group consisting of SEQ ID NO:3 and SEQ ID NO:4.

In some embodiments, the adapters are attached via enzyme ligation.

In some embodiments, the sample nucleic acids are nucleic acids from a human biological sample. In some embodiments, the biological sample is a urine, sputum, vaginal fluid, sperm, blood or synovial fluid sample Kits are also provided that comprise at least one of the oligonucleotide primers selected from the group consisting of SEQ ID NOs 1-335.

In some embodiments, the primers in a kit as disclosed herein further comprise a multiplex identifier sequence, a tag sequence and/or an adapter sequence. In some embodiments, one primer of a primer pair comprises an MID and both primers in a primer pair comprise adapter sequences. A forward primer and a reverse primer may comprise different adapter sequences. In some embodiments, the adapter sequence is selected from the group consisting of SEQ ID NO: 1 and SEQ ID NO:2. In some embodiments, the primers further comprise a multiplex identifier sequence. In some embodiments, the primers comprises a tag sequence specific for the microbial amplicon. In some embodiments, the tag sequence is selected from the group consisting of SEQ ID NO:3 and SEQ ID NO:4.

BRIEF DESCRIPTION OF THE FIGURES

FIG. 3 differs from FIG. 2 in that the adapters are attached in the opposite orientation.

DETAILED DESCRIPTION OF THE INVENTION

Definitions

Figure 1:
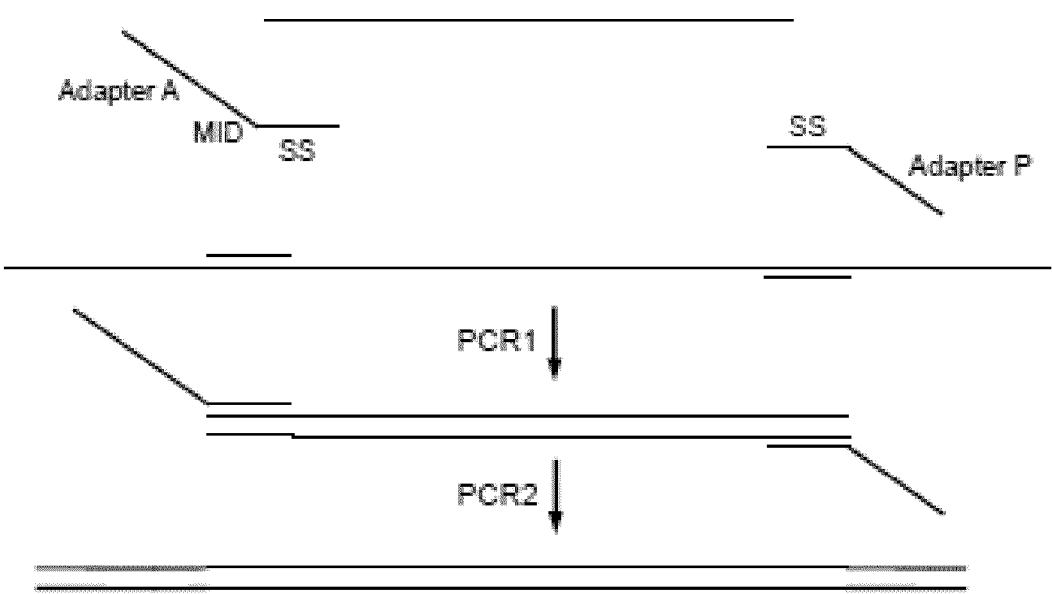
FIG. 1 depicts direct detection of a microbial agent using primers comprising an adapter sequence (Adapter A or Adapter P) and a target specific sequence (SS), with or without a multiplex identifier (MID). Microbial amplicons are generated in a first amplification reaction (PCR1) using primers comprising a target specific sequence (SS). Adapters are attached in a second amplification reaction (PCR2) using the primers comprising an adapter sequence (Adapter A or Adapter P) and a target specific sequence (SS), with or without a multiplex identifier (MID).
Figure 2:
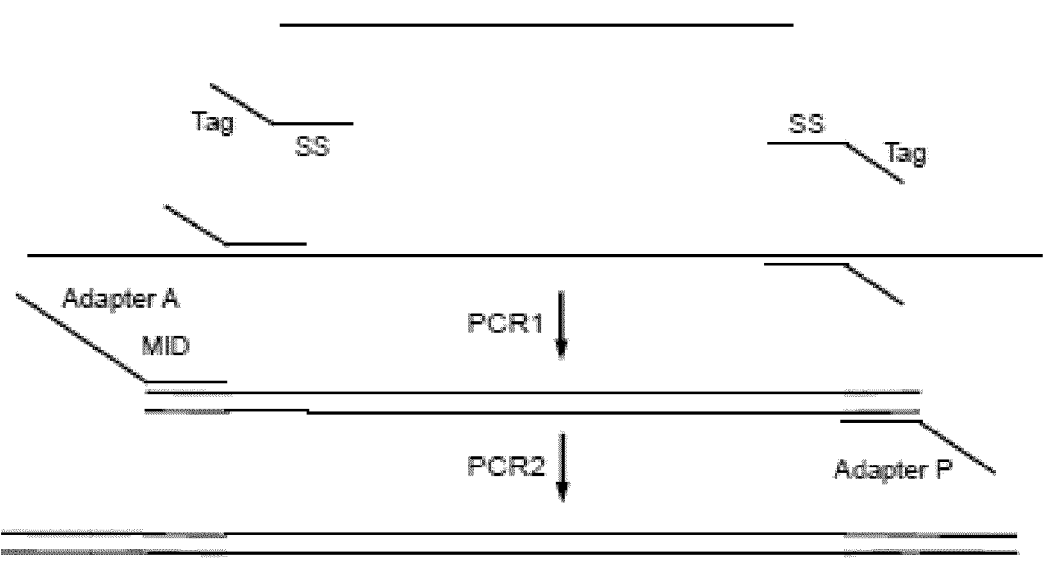
FIG. 2 depicts direct detection of a microbial agent using (i) primers comprising a target specific sequence (SS) and a tag (Tag) and (ii) primers comprising an adapter sequence (Adapter A or Adapter P) and the Tag sequence, with or without a multiplex identifier (MID). Microbial amplicons are generated in a first amplification reaction (PCR1) using primers comprising a target specific sequence (SS) and a tag (Tag). Adapters are attached in a second amplification reaction (PCR2) using the primers comprising an adapter sequence (Adapter A or Adapter P) and the Tag sequence, with or without a multiplex identifier (MID).
Figure 3:
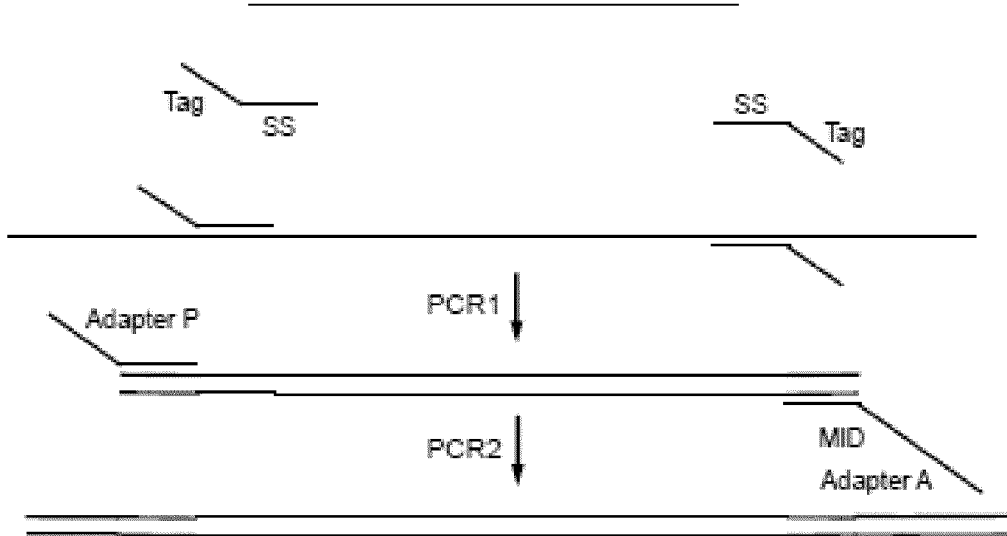
FIG. 3 depicts direct detection of a microbial agent with bi-directional sequencing using (i) primers comprising a target specific sequence (SS) and a tag (Tag) and (ii) primers comprising an adapter sequence (Adapter A or Adapter P) and the Tag sequence, with or without a multiplex identifier (MID).
Figure 4:
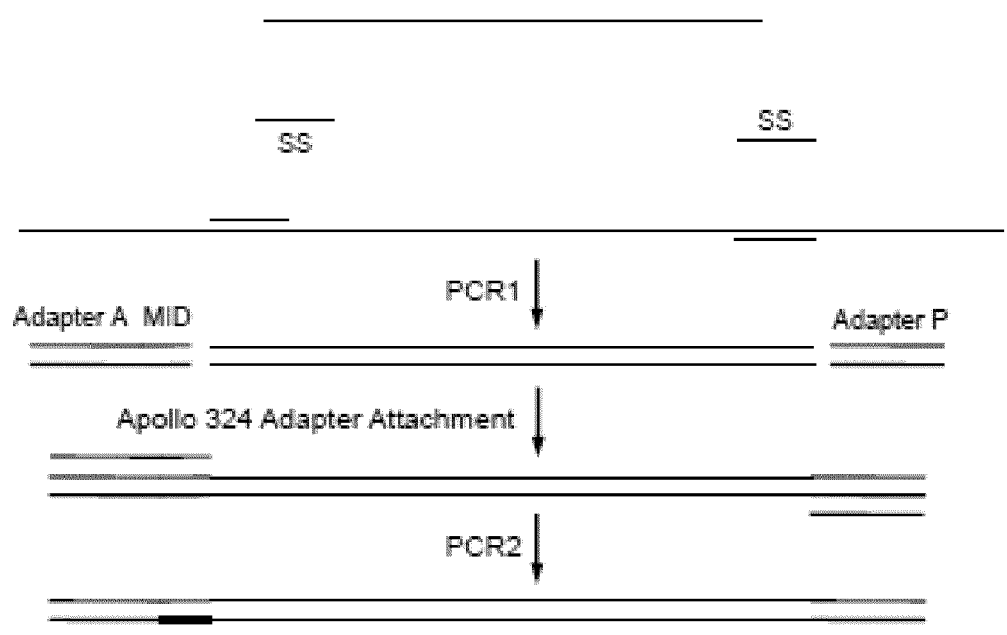
FIG. 4 depicts direct detection of a microbial agent using primers comprising a target specific sequence (SS) in a first amplification reaction (PCR1) and attaching a double stranded adapter sequence (Adapter A or Adapter P), with or without a multiplex identifier (MID), to the microbial amplicon using enzyme ligation (Apollo 324 Adapter Attachment). A second amplification reaction can be performed (PCR1) to further amplify the adapter-tagged amplicon.

The term "amplify" as used herein with respect to nucleic acid sequences, refers to methods that increase the representation of a population of nucleic acid sequences in a sample. Nucleic acid amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(1 1):E54-E54; Hafner et al., Biotechniques 2001 April; 30(4):852-6, 858, 860 passim; Zhong et al., Biotechniques 2001 April; 30(4): 852-6, 858, 860.

A "nucleic acid" as used herein refers to a nucleic acid that contains a sequence of a microbial gene, mRNA, cDNA or a portion of such a sequence. A nucleic acid may contain the coding region. A nucleic acid may be genomic DNA, cDNA, single stranded DNA or mRNA. In some embodiments, only a single strand of a sample nucleic acid is amplified and/or sequenced. In some embodiments both strands of double stranded DNA are amplified and sequenced. A nucleic acid may be present in a sample, such as a biological sample, or it may be isolated from the sample.

The term "sense strand" as used herein means the strand of double-stranded DNA (dsDNA) that includes at least a portion of a coding sequence of a functional protein. "Antisense strand" means the strand of dsDNA that is the reverse complement of the sense strand.

The terms "complementary" or "complementarity" as used herein with reference to polynucleotides (i.e., a sequence of nucleotides such as an oligonucleotide or a target nucleic acid) refers to the base-pairing rules. The complement of a nucleic acid sequence as used herein refers to nucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5." Certain bases not commonly found in natural nucleic acids may be included in the nucleic acids described herein; these include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be a sequence of RNA complementary to the DNA sequence or its complement sequence, and can also be a cDNA.

The term "substantially complementary" as used herein means that two sequences hybridize under stringent hybridization conditions. The skilled artisan will understand that substantially complementary sequences need not hybridize along their entire length. In particular, substantially complementary sequences may comprise a contiguous sequence of bases that do not hybridize to a target sequence, positioned 3' or 5' to a contiguous sequence of bases that hybridize under stringent hybridization conditions to a target sequence.

The term "hybridize" as used herein refers to a process where two complementary nucleic acid strands anneal to each other under appropriately stringent conditions. Hybridizations are typically and preferably conducted with probe-length nucleic acid molecules, preferably 20-100 nucleotides in length, more preferably 18-50 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J. In some embodiments, specific hybridization occurs under stringent hybridization conditions.

The term "stringent hybridization conditions" as used herein refers to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5×Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "dosage" or "gene dosage" refers to the number of copies of a gene, or portions of a gene, present in a sample.

The term "primer" as used herein means a sequence of nucleic acid, including DNA, which hybridizes to a substantially complementary target sequence and is recognized by DNA polymerase to begin DNA replication. The term primer as used herein includes all forms of primers that may be synthesized, including peptide nucleic acid primers, locked nucleic acid primers, phosphorothioate modified primers, labeled primers, and the like.

The term "forward primer" as used herein means a primer that anneals to the anti-sense strand of dsDNA. A "reverse primer" anneals to the sense-strand of dsDNA.

The term "specific" as used herein in reference to an oligonucleotide primer means that the primer hybridization sequence of the primer has at least 12 bases of sequence identity with a portion of the nucleic acid to be amplified when the oligonucleotide and the nucleic acid are aligned. A primer that is specific for a nucleic acid is one that, under the stringent hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity.

The term "flanking" as used herein with regard to primers means that a primer hybridizes to a target nucleic acid adjoining a region of interest sought to be amplified on the target. The skilled artisan will understand that preferred primers are pairs of primers that hybridize 5' from a region of interest, one on each strand of a target double stranded DNA molecule, such that nucleotides may be added to the 3' end of the primer by a suitable DNA polymerase. Primers that flank an exon are generally designed not to anneal to the exon sequence but rather to anneal to sequence that adjoins the exon (e.g., intron sequence). However, in some cases, an amplification primer may be designed to anneal to the exon sequence.

"Sequencing depth" or "read depth" as used herein refers to the number of times a sequence has been sequenced (i.e., the depth of sequencing). As an example, read depth can be determined by aligning multiple sequencing run results and counting the start position of reads in nonoverlapping windows of a certain size (e.g., 100 bp). Copy number variation can be determined based on read depth using methods known in the art. For example, using a method described in Yoon et al., Genome Research 2009 September; 19(9): 1586-1592; Xie et al., BMC Bioinformatics 2009 Mar. 6; 10:80; or Medvedev et al., Nature Methods 2009 November; 6(11 Suppl):S13-20. Use of this type of method and analysis is referred to as a "read depth approach."

"Coverage depth" refers to the number of nucleotides from sequencing reads that are mapped to a given position.

The term "isolated" as used herein with respect to a nucleic acid (e.g., RNA, DNA or a mixed polymer) is one which is substantially separated from other cellular components which naturally accompany such nucleic acid. The term embraces a nucleic acid sequence which has been removed from its naturally occurring environment, and includes recombinant or cloned DNA isolates, oligonucleotides, and chemically synthesized analogs or analogs biologically synthesized by heterologous systems.

The term "substantially pure" as used herein means a nucleic acid, represents more than 50% of the nucleic acid in a sample. The nucleic acid sample may exist in solution or as a dry preparation.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced there from.

The term "non-coding sequence" as used herein means a sequence of a nucleic acid or its complement, or a part thereof, which is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

The term "about" as used herein means in quantitative terms plus or minus 10%.

Methods

Described herein are methods for direct detection of one or more microbial agents (i.e., microbial agent(s)) in a sample. Direct detection refers to identifying microbial agent(s) in a sample without culturing the sample. Culturing as used herein refers to any technique in which microbial agents in a sample are sustained and/or expanded in vitro, for example, using media and/or growth conditions. In some embodiments, direct detection refers to identifying a mixture of different microbial agents in a sample, such as a mixture of different bacteria, a mixture of different fungi, and a mixture of bacterium/bacteria and fungus/fungi.

In some embodiments, methods for direct detection include extracting nucleic acid from a sample without separating different types of nucleic acid, such as nucleic acid from different types of microbial agents. In some embodiments, methods for direct detection include identifying microbial agent(s) in a sample after extracting nucleic acid from the sample. In specific embodiments, direct detection includes identifying microbial agent(s) in a mammalian biological sample, such as a human biological sample, after extracting nucleic acid from the sample. In other embodiments, direct detection includes identifying microbial agent(s) in a human biological sample after human nucleic acid has been separated and removed from extracted nucleic acid.

Microbial Agent

A microbial agent as used herein is any microorganism. In some embodiments, the microbial agent is a bacterium. In other embodiments, the microbial agent is a fungus. In some embodiments, the microbial agent is a species selected from the group consisting of *Mycobacterium, Streptococcus, Staphylococcus, Burkholderia, Enterococcus*, and *Pseudomonas*.

A target sequence as described herein may represent one or more individual exon(s) or portion(s) of exon(s) of a microbial gene or one or more portions of a microbial mRNA. A target sequence also may include the promoter region and/or one or more introns of a microbial agent gene.

In some embodiments the target sequence represents the entire gene or the entire coding region. In some embodiments, the target sequence represents the entire coding region and at least one intron or a portion thereof and an adjacent region located immediately upstream (in the 5' direction) of the coding sequence. The adjacent, upstream region may consist of from about 100 nucleotides up to about 500, 750, 1000, 1100, or 1200 nucleotides of the sequence located immediately upstream of the coding sequence. In some embodiments, the adjacent, upstream region comprises all or a portion of the promoter sequence.

Sample

A sample as used herein contains nucleic acid of microbial agent(s) in, or isolated from, any source. In some embodiments, the sample is a biological sample from a mammal. In specific embodiments, the mammal is a human.

In some embodiments, the biological sample is a body fluid or a tissue sample. In some embodiments the biological sample consists or comprises blood, plasma, sera, urine, feces, epidermal sample, vaginal sample, skin sample, cheek swab, sperm, amniotic fluid, cultured cells, bone marrow sample and/or chorionic villi, cultured cells, and combinations thereof.

In some embodiments, the biological sample is a fixed or frozen tissue. In some embodiments, the biological sample is whole blood of about 0.5 to 5 ml collected with EDTA, ACD or heparin as anti-coagulant. In some embodiments, the biological sample is amniotic fluid of 10-15 ml, cultured cells which are 80-100% confluent in two T-25 flasks, or 25 mg of chorionic villi.

In some embodiments, the sample contains one or more microbial agents. In some embodiments, the sample contains multiple microbial agents. In some embodiments, the sample contains a mixture of bacteria. In other embodiments, the sample contains a mixture of fungi. In other embodiments, the sample contains a mixture of bacterium/bacteria and fungus/fungi.

Processing methods to release or otherwise make available a nucleic acid for detection are well known in the art and may include steps of nucleic acid manipulation, e.g., preparing a cDNA by reverse transcription of RNA from a biological sample. In some embodiments, a sample taken from a patient is extracted using the MagNA Pure LC instrument or an equivalent tabletop instrument that performs rapid, cross-contamination-free preparation of nucleic acids and PCR setup. The instrument may utilize magnetic-bead technology and may be equipped with a robotic system and automatically isolates any type of nucleic acid. It further may be capable of processing up to 32 different samples in one batch. The enables consistent isolation of high-quality DNA or RNA.

Adapter Sequence

An adapter sequence (also referred to as a sequencing adapter) is ligated to the 5' end of the target specific sequence portion of the primer. This sequencing adapter is a short oligonucleotide of known sequence that can provide a priming site for both amplification and sequencing of the adjoining, unknown nucleic acid. As such, adapters allow binding of a fragment to a flow cell for high throughput, massively parallel sequencing, as described herein. Any adapter sequence may be included in a primer used in the present invention.

In some embodiments, all forward amplicons (i.e., amplicons extended from forward primers that hybridized with antisense strands of a target segment) contain the same adapter sequence. In some embodiments when double stranded sequencing is performed, all forward amplicons contain the same adapter sequence and all reverse amplicons (i.e., amplicons extended from reverse primers that hybridized with sense strands of a target segment) contain an adapter sequence that is different from the adapter sequence of the forward amplicons.

In some embodiments, the "forward" adapter sequence consists of or comprises: CCATCT-CATCCCTGCGTGTCTCCGACTCAG (SEQ ID NO:1) or a sequence 90%, 95%, 97%, 98%, or 99% identical to SEQ ID NO:1. and the reverse adapter sequence consists of or comprises CCTCTCTATGGGCAGTCGGTGAT (SEQ ID NO:2) or a sequence 90%, 95%, 97%, 98%, or 99% identical to SEQ ID NO:2. These sequences are provided in Table 1.

Other adapter sequences are known in the art. Some manufacturers recommend specific adapter sequences for use with the particular sequencing technology and machinery that they offer.

In some embodiments, when adapter-ligated and/or indexed primers are employed to amplify a target segment, the adapter sequence and/or index sequence gets incorporated into the amplicon (along with the target-specific primer sequence) during amplification. Therefore, the resulting amplicons are sequencing-competent and do not require the traditional library preparation protocol. Moreover, the presence of the index tag permits the differentiation of sequences from multiple sample sources.

In some embodiments, sequencing templates (amplicons) are prepared by emulsion-based clonal amplification of target segments using specialized fusion primers (containing an adapter sequence) and capture beads. A single adapter-bound fragment is attached to the surface of a bead, and an oil emulsion containing necessary amplification reagents is formed around the bead/fragment component. Parallel amplification of millions of beads with millions of single strand fragments produces a sequencer-ready library.

In some embodiments, the amplicons constituting the adapter-tagged (and, optionally, indexed) amplicon library are produced by polymerase chain reaction (PCR). In some embodiments, the amplicon library is generated using a multiplexed PCR approach, such as that disclosed in U.S. Pat. No. 8,092,996, incorporated by reference herein in its entirety.

In other embodiments, each nucleic acid target segment may be amplified with non-adapter-ligated and/or non-indexed primers and a sequencing adapter and/or an index sequence may be subsequently ligated to each of the resulting amplicons.

In some embodiments, sequencing by ligation method using a DNA ligase is applied to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method can utilize Life Technologies' SOLiD™ sequencers.

Multiplex Identifier

In some cases, amplicons from a single sample source further comprise an identical index sequence (also referred to as an index tag, a "barcode" or a multiplex identifier (MID)). In some cases, indexed amplicons are generated using primers (for example, forward primers and/or reverse primers) containing the index sequence. Such indexed primers may be included during library preparation as a "barcoding" tool to identify specific amplicons as originating from a particular sample source. Indexed amplicons from more than one sample source are quantified individually and then pooled prior to sequencing. As such, the use of index sequences permits multiple samples (i.e., samples from more than one sample source) to be pooled per sequencing run and the sample source subsequently ascertained based on the index sequence. Table 1 provides examples of MID sequences used in the methods described herein.

In some embodiments, amplicons from more than one sample source are pooled prior to high throughput sequencing. "Multiplexing" is the pooling of multiple adapter-tagged and indexed libraries into a single sequencing run. When indexed primer sets are used, this capability can be exploited for comparative studies. In some embodiments, amplicon libraries from up to 48 separate sources are pooled prior to sequencing.

High Throughput, Massively Parallel Sequencing

High throughput, massively parallel sequencing refers to sequencing methods that can generate multiple sequencing reactions of clonally amplified molecules and of single nucleic acid molecules in parallel. This allows increased throughput and yield of data. These methods are also known in the art as next generation sequencing (NGS) methods. NGS methods include, for example, sequencing-by-synthesis using reversible dye terminators, and sequencing-by-ligation.

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing.

Non-limiting examples of commonly used NGS platforms include Apollo 324™ NGS Library Prep System (IntengenX, Pleasanton, United States), Ion Torrent™ (Life Technologies, Carlsbad, Calif.), miRNA BeadArray (Illumina, Inc.), Roche 454™ GS FLX™-Titanium (Roche Molecular Diagnostics, Germany), and ABI SOLiD™ System (Applied Biosystems, Foster City, Calif.). Following the production of an adapter tagged and, optionally indexed, amplicon library, the amplicons are sequenced using high throughput, massively parallel sequencing.

Kit and Primer(s)

The direct detection methods as described herein can be performed using a kit comprising any one or more of the following components: universal primer(s) (e.g., 16S rDNA and ITS rDNA); primer(s), including primer(s) comprising one or more of a target specific sequence, adapter sequence, MID, and tag; dNTP; and other components for amplifying nucleic acid, such as by PCR (including via high throughput, massively parallel sequencing). In some embodiments, the kit comprises components to extract human nucleic acid from a sample.

In some embodiments, the kit comprises any one or more of SEQ ID NOs: 1-335, as listed in Tables 1-10. The kit can include a primer or primer pair comprising any combination of the sequences listed in Tables 1-10, with or without additional nucleic acid(s). For example, SEQ ID NO:23 is a primer consisting of SEQ ID NO: 1 (Adapter A sequence) and SEQ ID NO:5 (MID1). However, a primer or primer pair as described herein can include SEQ ID NO:1 and SEQ ID NO:5 with additional nucleic acid(s) between the two sequences or flanking one or both sequences. In some embodiments, a primer or primer pair as described herein comprises a spacer between two or more of SEQ ID NOs: 1-335. Spacers are known in the art.

TABLE 1

| | Adapter, Tag, and Multiplex Identifier Sequences | |
| --- | --- | --- |
| SEQ ID NO: | Name | Sequence |
| | Adapter Sequences | |
| 1 | Adapter A | CCATCTCATCCCTGCGTGTCTCCGACTCAG |
| 2 | Adapter P | CCTCTCTATGGGCAGTCGGTGAT |

TABLE 1-continued

Adapter, Tag, and Multiplex Identifier Sequences

| SEQ ID NO: | Name | Sequence |
|---|---|---|

Tag Sequences

| | | |
|---|---|---|
| 3 | Forward Tag | ACACTGACGACATGGTTCTACA |
| 4 | Reverse Tag | TACGGTAGCAGAGACTTGGTCT |

Multiplex Index Sequences

| | | |
|---|---|---|
| 5 | MID1 | ACGAGTGCGT |
| 6 | MID2 | ACGCTCGACA |
| 7 | MID3 | AGACGCACTC |
| 8 | MID4 | AGCACTGTAG |
| 9 | MID5 | ATCAGACACG |
| 10 | MID6 | ATATCGCGAG |
| 11 | MID7 | CGTGTCTCTA |
| 12 | MID8 | CTCGCGTGTC |
| 13 | MID9 | TAGTATCAGC |
| 14 | MID10 | TCTCTATGCG |
| 15 | MID11 | TGATACGTCT |
| 16 | MID12 | TACTGAGCTA |
| 17 | MID13 | CATAGTAGTG |
| 18 | MID14 | CGAGAGATAC |
| 19 | MID15 | ATACGACGTA |
| 20 | MID16 | TCACGTACTA |
| 21 | MID17 | CGTCTAGTAC |
| 22 | MID18 | TCTACGTAGC |

Primers with Adapter and Multiplex Index Sequences

| | | |
|---|---|---|
| 23 | PGMA MID1 | CCATCTCATCCCTGCGTGTCTCCGACTCAG ACGAGTGCGT |
| 24 | PGMA MID2 | CCATCTCATCCCTGCGTGTCTCCGACTCAG ACGCTCGACA |
| 25 | PGMA MID3 | CCATCTCATCCCTGCGTGTCTCCGACTCAG AGACGCACTC |
| 26 | PGMA MID4 | CCATCTCATCCCTGCGTGTCTCCGACTCAG AGCACTGTAG |
| 27 | PGMA MID5 | CCATCTCATCCCTGCGTGTCTCCGACTCAG ATCAGACACG |
| 28 | PGMA MID6 | CCATCTCATCCCTGCGTGTCTCCGACTCAG ATATCGCGAG |
| 29 | PGMA MID7 | CCATCTCATCCCTGCGTGTCTCCGACTCAG CGTGTCTCTA |
| 30 | PGMA MID8 | CCATCTCATCCCTGCGTGTCTCCGACTCAG CTCGCGTGTC |
| 31 | PGMA MID9 | CCATCTCATCCCTGCGTGTCTCCGACTCAG TAGTATCAGC |
| 32 | PGMA MID10 | CCATCTCATCCCTGCGTGTCTCCGACTCAG TCTCTATGCG |
| 33 | PGMA MID11 | CCATCTCATCCCTGCGTGTCTCCGACTCAG TGATACGTCT |
| 34 | PGMA MID12 | CCATCTCATCCCTGCGTGTCTCCGACTCAG TACTGAGCTA |
| 35 | PGMA MID13 | CCATCTCATCCCTGCGTGTCTCCGACTCAG CATAGTAGTG |
| 36 | PGMA MID14 | CCATCTCATCCCTGCGTGTCTCCGACTCAG CGAGAGATAC |

TABLE 1-continued

| SEQ ID NO: | Name | Sequence |
|---|---|---|
| | | Adapter, Taq, and Multiplex Identifier Sequences |
| 37 | PGMA MID15 | CCATCTCATCCCTGCGTGTCTCCGACTCAG ATACGACGTA |
| 38 | PGMA MID16 | CCATCTCATCCCTGCGTGTCTCCGACTCAG TCACGTACTA |
| 39 | PGMA MID1 Comp | ACGCACTCGT CTGAGTCGGAGACACGCAGGGATGAGATGG |
| 40 | PGMA MID2 Comp | TGTCGAGCGT CTGAGTCGGAGACACGCAGGGATGAGATGG |
| 41 | PGMA MID3 Comp | GAGTGCGTCT CTGAGTCGGAGACACGCAGGGATGAGATGG |
| 42 | PGMA MID4 Comp | CTACAGTGCT CTGAGTCGGAGACACGCAGGGATGAGATGG |
| 43 | PGMA MID5 Comp | CGTGTCTGAT CTGAGTCGGAGACACGCAGGGATGAGATGG |
| 44 | PGMA MID6 Comp | CTCGCGATAT CTGAGTCGGAGACACGCAGGGATGAGATGG |
| 45 | PGMA MID7 Comp | TAGAGACACG CTGAGTCGGAGACACGCAGGGATGAGATGG |
| 46 | PGMA MID8 Comp | GACACGCGAG CTGAGTCGGAGACACGCAGGGATGAGATGG |
| 47 | PGMA MID9 Comp | GCTGATACTA CTGAGTCGGAGACACGCAGGGATGAGATGG |
| 48 | PGMA MID10 Comp | CGCATAGAGA CTGAGTCGGAGACACGCAGGGATGAGATGG |
| 49 | PGMA MID11 Comp | AGACGTATCA CTGAGTCGGAGACACGCAGGGATGAGATGG |
| 50 | PGMA MID12 Comp | TAGCTCAGTA CTGAGTCGGAGACACGCAGGGATGAGATGG |
| 51 | PGMA MID13 Comp | CACTACTATG CTGAGTCGGAGACACGCAGGGATGAGATGG |
| 52 | PGMA MID14 Comp | GTATCTCTCG CTGAGTCGGAGACACGCAGGGATGAGATGG |
| 53 | PGMA MID15 Comp | TACGTCGTAT CTGAGTCGGAGACACGCAGGGATGAGATGG |
| 54 | PGMA MID16 Comp | TAGTACGTGA CTGAGTCGGAGACACGCAGGGATGAGATGG |
| | | PCR2 Forward Primers (Primers with Adapter A, MID, and Forward Tag) |
| 55 | PGMA MID1 FT | CCATCTCATCCCTGCGTGTCTCCGACTCAG ACGAGTGCGT ACACTGACGACATGGTTCTACA |
| 56 | PGMA MID2 FT | CCATCTCATCCCTGCGTGTCTCCGACTCAG ACGCTCGACA ACACTGACGACATGGTTCTACA |
| 57 | PGMA MID3 FT | CCATCTCATCCCTGCGTGTCTCCGACTCAG AGACGCACTC ACACTGACGACATGGTTCTACA |
| 58 | PGMA MID4 FT | CCATCTCATCCCTGCGTGTCTCCGACTCAG AGCACTGTAG ACACTGACGACATGGTTCTACA |
| 59 | PGMA MID5 FT | CCATCTCATCCCTGCGTGTCTCCGACTCAG ATCAGACACG ACACTGACGACATGGTTCTACA |
| 60 | PGMA MID6 FT | CCATCTCATCCCTGCGTGTCTCCGACTCAG ATATCGCGAG ACACTGACGACATGGTTCTACA |
| 61 | PGMA MID7 FT | CCATCTCATCCCTGCGTGTCTCCGACTCAG CGTGTCTCTA ACACTGACGACATGGTTCTACA |
| 62 | PGMA MID8 FT | CCATCTCATCCCTGCGTGTCTCCGACTCAG CTCGCGTGTC ACACTGACGACATGGTTCTACA |
| 63 | PGMA MID9 FT | CCATCTCATCCCTGCGTGTCTCCGACTCAG TAGTATCAGC ACACTGACGACATGGTTCTACA |
| 64 | PGMA MID10 FT | CCATCTCATCCCTGCGTGTCTCCGACTCAG TCTCTATGCG ACACTGACGACATGGTTCTACA |
| 65 | PGMA MID11 FT | CCATCTCATCCCTGCGTGTCTCCGACTCAG TGATACGTCT ACACTGACGACATGGTTCTACA |
| 66 | PGMA MID12 FT | CCATCTCATCCCTGCGTGTCTCCGACTCAG TACTGAGCTA ACACTGACGACATGGTTCTACA |

TABLE 1-continued

Adapter, Tag, and Multiplex Identifier Sequences

| SEQ ID NO: | Name | Sequence |
|---|---|---|
| 67 | PGMA MID13 FT | CCATCTCATCCCTGCGTGTCTCCGACTCAG CATAGTAGTG ACACTGACGACATGGTTCTACA |
| 68 | PGMA MID14 FT | CCATCTCATCCCTGCGTGTCTCCGACTCAG CGAGAGATAC ACACTGACGACATGGTTCTACA |
| 69 | PGMA MID15 FT | CCATCTCATCCCTGCGTGTCTCCGACTCAG ATACGACGTA ACACTGACGACATGGTTCTACA |
| 70 | PGMA MID16 FT | CCATCTCATCCCTGCGTGTCTCCGACTCAG TCACGTACTA ACACTGACGACATGGTTCTACA |

Primer with Adapter P and Reverse Tag

| 71 | Primer P RT | CCTCTCTATGGGCAGTCGGTGAT TACGGTAGCAGAGACTTGGTCT |
|---|---|---|

PCR2 Reverse Primers
(Primers with Adapter A, MID, and Reverse Tag)

| 72 | PGMA MID1 RT | CCATCTCATCCCTGCGTGTCTCCGACTCAG ACGAGTGCGT TACGGTAGCAGAGACTTGGTCT |
|---|---|---|
| 73 | PGMA MID2 RT | CCATCTCATCCCTGCGTGTCTCCGACTCAG ACGCTCGACA TACGGTAGCAGAGACTTGGTCT |
| 74 | PGMA MID3 RT | CCATCTCATCCCTGCGTGTCTCCGACTCAG AGACGCACTC TACGGTAGCAGAGACTTGGTCT |
| 75 | PGMA MID4 RT | CCATCTCATCCCTGCGTGTCTCCGACTCAG AGCACTGTAG TACGGTAGCAGAGACTTGGTCT |
| 76 | PGMA MID5 RT | CCATCTCATCCCTGCGTGTCTCCGACTCAG ATCAGACACG TACGGTAGCAGAGACTTGGTCT |
| 77 | PGMA MID6 RT | CCATCTCATCCCTGCGTGTCTCCGACTCAG ATATCGCGAG TACGGTAGCAGAGACTTGGTCT |
| 78 | PGMA MID7 RT | CCATCTCATCCCTGCGTGTCTCCGACTCAG CGTGTCTCTA TACGGTAGCAGAGACTTGGTCT |
| 79 | PGMA MID8 RT | CCATCTCATCCCTGCGTGTCTCCGACTCAG CTCGCGTGTC TACGGTAGCAGAGACTTGGTCT |
| 80 | PGMA MID9 RT | CCATCTCATCCCTGCGTGTCTCCGACTCAG TAGTATCAGC TACGGTAGCAGAGACTTGGTCT |
| 81 | PGMA MID10 RT | CCATCTCATCCCTGCGTGTCTCCGACTCAG TCTCTATGCG TACGGTAGCAGAGACTTGGTCT |
| 82 | PGMA MID11 RT | CCATCTCATCCCTGCGTGTCTCCGACTCAG TGATACGTCT TACGGTAGCAGAGACTTGGTCT |
| 83 | PGMA MID12 RT | CCATCTCATCCCTGCGTGTCTCCGACTCAG TACTGAGCTA TACGGTAGCAGAGACTTGGTCT |
| 84 | PGMA MID13 RT | CCATCTCATCCCTGCGTGTCTCCGACTCAG CATAGTAGTG TACGGTAGCAGAGACTTGGTCT |
| 85 | PGMA MID14 RT | CCATCTCATCCCTGCGTGTCTCCGACTCAG CGAGAGATAC TACGGTAGCAGAGACTTGGTCT |
| 86 | PGMA MID15 RT | CCATCTCATCCCTGCGTGTCTCCGACTCAG ATACGACGTA TACGGTAGCAGAGACTTGGTCT |
| 87 | PGMA MID16 RT | CCATCTCATCCCTGCGTGTCTCCGACTCAG TCACGTACTA TACGGTAGCAGAGACTTGGTCT |

Primer with Adapter P and Forward Tag

| 88 | Primer P FT | CCTCTCTATGGGCAGTCGGTGAT ACACTGACGACATGGTTCTACA |
|---|---|---|

TABLE 2

16S Sequences

| SEQ ID NO: | Name | Sequence | |
|---|---|---|---|
| | 16S V2 Set 2 | | |
| 89 | 16S V2 F101a | GGCGGACGGGTGAGTAA | |
| 90 | 16S V2 F101b | GGCGAACGGGTGAGTAA | |
| 91 | 16S V2 F101c | GGCGGACGGGTGAGTAA | |
| 92 | 16S V2 F101d | GGCGGATGGGTGAGTAA | *Lactobacillus* |
| 93 | 16S V2 F101e | GGCAAACGGGTGAGTAA | *Megasphaera* |
| 94 | 16S V2 F101f | GGCGAACGGGCGAGTAA | *Mobiluncus* |
| 95 | 16S V2 F101g | GGCGAACGGCTGAGTAA | *Atopobium* |
| 96 | 16S V2 R356a | CACTGCTGCCTCCCGTAG | |
| 97 | 16S V2 R356b | TACTGCTGCCTCCCGTAG | |
| | 16S V3 Set 2 | | |
| 98 | 16S V3 F323a | GACACGGTCCAGACTCCTAC | |
| 99 | 16S V3 F323b | GACACGGCCCAGACTCCTAC | |
| 100 | 16S V3 F323c | GACACGGTCCAAACTCCTAC | *Bacillus* |
| 101 | 16S V3 F323d | GACACGGCCCAAACTCCTAC | *Lactobacillus* |
| 102 | 16S V3 F323e | GATACGGCCCAGACTCCTAC | Myco, Mob, Gard |
| 103 | 16S V3 R531a | ATTACCGCGGCTGCTG | |
| | PCR1 V2 (Tag, Sequence Specific) | | |
| 104 | Tag V2 F101a | ACACTGACGACATGGTTCTA CAGGCGGACGGGTGAGTAA | |
| 105 | Tag V2 F101b | ACACTGACGACATGGTTCTA CAGGCGAACGGGTGAGTAA | |
| 106 | Tag V2 F101c | ACACTGACGACATGGTTCTA CAGGCGCACGGGTGAGTAA | |
| 107 | Tag V2 F101d | ACACTGACGACATGGTTCTA CAGGCGGATGGGTGAGTAA | |
| 108 | Tag V2 F101e | ACACTGACGACATGGTTCTA CAGGCAAACGGGTGAGTAA | |
| 109 | Tag V2 F101f | ACACTGACGACATGGTTCTA CAGGCGAACGGGCGAGTAA | |
| 110 | Tag V2 F101g | ACACTGACGACATGGTTCTA CAGGCGAACGGCTGAGTAA | |
| 111 | Tag V2 R356a | TACGGTAGCAGAGACTTGGT CTCACTGCTGCCTCCCGTAG | |
| 112 | Tag V2 R356b | TACGGTAGCAGAGACTTGGT CTTACTGCTGCCTCCCGTAG | |
| | PCR1 V3 (Tag, Sequence Specific) | | |
| 113 | Tag V3 F323a | ACACTGACGACATGGTTCTA CAGACACGGTCCAGACTCCT AC | |
| 114 | Tag V3 F323b | ACACTGACGACATGGTTCTA CAGACACGGCCCAGACTCCT AC | |

TABLE 2-continued

16S Sequences

| SEQ ID NO: | Name | Sequence |
|---|---|---|
| 115 | Tag V3 F323c | ACACTGACGACATGGTTCTA CAGACACGGTCCAAACTCCT AC |
| 116 | Tag V3 F323d | ACACTGACGACATGGTTCTA CAGACACGGCCCAAACTCCT AC |
| 117 | Tag V3 F323e | ACACTGACGACATGGTTCTA CAGATACGGCCCAGACTCCT AC |
| 118 | Tag V3 R531a | TACGGTAGCAGAGACTTGGT CTATTACCGCGGCTGCTG |

TABLE 3

ITS Sequences

| SEQ ID NO: | Name | Sequence |
|---|---|---|
| | ITS Sequences F and R Primer Pairs | |
| 119 | ITS1Fb | AAACTCGGTCATTTAGAGGAAGTAA |
| 120 | ITSR513 | GATGCCGGAACCAAGAGAT |
| 121 | ITSF329 | AACCTCCCACCCGTGTTTAT |
| 122 | ITSR533 | ATTTCGCTGCGTTCTTCATC |
| 123 | ITS1Fb | AAACTCGGTCATTTAGAGGAAGTAA |
| 124 | ITS2b | GCTGCGTTCTTCATCGATG |
| 125 | ITSF569 | ATCGAGTCTTTGAACGCACA |
| 126 | ITSR820 | CCTACCTGATCCGAGGTCAA |
| 127 | ITSF570 | TCGAGTCTTTGAACGCACAT |
| 128 | ITSR828 | CGGGTATCCCTACCTGATCC |
| | ITS Reading Set (Adapter A, MID or Adapter P) | |
| 129 | ITSPGM1FbA MID1 | CCATCTCATCCCTGCGTGTCTCCGAC<u>TCAG</u> ACGAGTGCGTAAACTCGGTCATTTAG<u>AGGA</u> AGTAA |
| 130 | ITSPGMR513P | CCTCTCTATGGGCAGTCGGTGAT GATGCCGGAACCAAGAGAT |
| 131 | TTSPGMF329A MID1 | CCATCTCATCCCTGCGTGTCTCCGAC<u>TCAG</u> ACGAGTGCGTAACCTCCCACCCGTG<u>TTTAT</u> |
| 132 | ITSPGMR533P | CCTCTCTATGGGCAGTCGGTGAT ATTTCGCTGCGTTCTTCATC |
| 133 | ITSPGM1FbA MID1 | CCATCTCATCCCTGCGTGTCTCCGAC<u>TCAG</u> ACGAGTGCGTAAACTCGGTCATTTAG<u>AGGA</u> AGTAA |
| 134 | ITSPGM2bP | CCTCTCTATGGGCAGTCGGTGAT GCTGCGTTCTTCATCGATG |
| 135 | ITSPGMF569A MID1 | CCATCTCATCCCTGCGTGTCTCCGAC<u>TCAG</u> ACGAGTGCGTATCGAGTCTTTGAAC<u>GCACA</u> |

TABLE 3-continued

| | | ITS Sequences |
|---|---|---|
| SEQ ID NO: | Name | Sequence |
| 136 | ITSPGMR820P | CCTCTCTATGGGCAGTCGGTGAT CCTACCTGATCCGAGGTCAA |
| 137 | ITSPGMF570A MID1 | CCATCTCATCCCTGCGTGTCTCCGAC<u>TCAG</u> ACGAGTGCGTTCGAGTCTTTGAACGCACAT |
| 138 | ITSPGMR828P | CCTCTCTATGGGCAGTCGGTGAT CGGGTATCCCTACCTGATCC |

TABLE 3-continued

| | | ITS Sequences |
|---|---|---|
| SEQ ID NO: | Name | Sequence |
| | | PCR1 (Tag, Sequence Specific) |
| 335 | Tag ITS1Fb | ACACTGACGACATGGTTCTACA AAACTCGGTCATTTAGAGGAAGTAA |
| 336 | Tag ITS2b | TACGGTAGCAGAGACTTGGTCT GCTGCGTTCTTCATCGATG |
| 337 | Tag ITSF569 | ACACTGACGACATGGTTCTACA ATCGAGTCTTTGAACGCACA |
| 338 | Tag ITSR820 | TACGGTAGCAGAGACTTGGTCT CCTACCTGATCCGAGGTCAA |

TABLE 4

| | | *Mycobacterium* Sequences | |
|---|---|---|---|
| SEQ ID NO: | Name | Sequence | Description |
| | | *Mycobacterium* Fragment 1 | |
| 139 | MycoPGMF2649 | GCAAGGTCACCCCGAAG | |
| 140 | MycoPGMR2924 | CGATGACGCCCTTGTTG | |
| 141 | MycoPGMF2648 | GGCAAGGTCACCCCGAAGG | |
| 142 | MycoPGMR2934 | AGGATCTTGCCGATGACG | |
| | | *Mycobacterium* Fragment 2 | |
| 143 | MycoPGM2F2898 | GACGCCACGGCAACAAG | |
| 144 | MycoPGM2F2899 | ACGCCACGGCAACAAG | |
| 145 | MycoPGM2R3337 | CAAGTGGTGCAGCTTCAGGATG | *Corynebacterium* |
| 146 | MycoPGM2R3337d | CARGTGGTGCAGCTTCAKGATG | |
| 147 | MycoPGM2R3169 | GGCGCCGTCGAACAC | |
| 148 | MycoPGM2R3169d | GGCRCCGTCGAACAC | |
| 149 | MycoPGM2R3169a | GGCACCGTCGAACAC | |
| 150 | MycoPGM2R3169b | GGCGCCGTCGAACAC | |
| | | *Mycobacterium* Fragment 3 | |
| 151 | MycoPGM2F3148 | CACCCCGGTGTTCGAC | |
| 152 | MycoPGM2R3391 | CTGGGTGATCATCGAGTACG | |
| | | Fragment 1 Forward Reading Set (Adapter A or Adapter P) | |
| 153 | MycoPGMF2649A | CCATCTCATCCCTGCGTGTCTCCGAC<u>TCAG</u> GCAAGGTCACCCCGAAG | |
| 154 | MycoPGMR2924P | CCTCTCTATGGGCAGTCGGTGAT CGATGACGCCCTTGTTG | |
| 155 | MycoPGMF2648A | CCATCTCATCCCTGCGTGTCTCCGAC<u>TCAG</u> GGCAAGGTCACCCCGAAGG | |
| 156 | MycoPGMR2934P | CCTCTCTATGGGCAGTCGGTGAT AGGATCTTGCCGATGACG | |

TABLE 4-continued

*Mycobacterium* Sequences

| SEQ ID NO: | Name | Sequence | Description |
|---|---|---|---|
| 157 | MycoPGMF2649A MID1 | CCATCTCATCCCTGCGTGTCTCCGACTCAG ACGAGTGCGT GCAAGGTCACCCCGAAG | |

Fragment 1 Reverse Reading Set (Adapter P or Adapter A)

| | | | |
|---|---|---|---|
| 158 | MycoPGMF2649P | CCTCTCTATGGGCAGTCGGTGAT GCAAGGTCACCCCGAAG | |
| 159 | MycoPGMR2924A | CCATCTCATCCCTGCGTGTCTCCGACTCAG CGATGACGCCCTTGTTG | |
| 160 | MycoPGMF2648P | CCTCTCTATGGGCAGTCGGTGAT GGCAAGGTCACCCCGAAGG | |
| 161 | MycoPGMR2934A | CCATCTCATCCCTGCGTGTCTCCGACTCAG AGGATCTTGCCGATGACG | |

Fragment 2 Forward Reading Set (Adapter A or Adapter P)

| | | | |
|---|---|---|---|
| 162 | MycoPGM2F2898A | CCATCTCATCCCTGCGTGTCTCCGACTCAG GACGCCACGGCAACAAG | |
| 163 | MycoPGM2F2899A | CCATCTCATCCCTGCGTGTCTCCGACTCAG ACGCCACGGCAACAAG | |
| 164 | MycoPGM2R3337P | CCTCTCTATGGGCAGTCGGTGAT CAAGTGGTGCAGCTTCAGGATG | |
| 165 | MycoPGM2R3337dP | CCTCTCTATGGGCAGTCGGTGAT CARGTGGTGCAGCTTCAKGATG | |
| 166 | MycoPGM2R3169P | CCTCTCTATGGGCAGTCGGTGAT GGCGCCGTCGAACAC | |
| 167 | MycoPGM2R3169dP | CCTCTCTATGGGCAGTCGGTGAT GGCRCCGTCGAACAC | |
| 168 | MycoPGM2F2898A MID1 | CCATCTCATCCCTGCGTGTCTCCGACTCAG ACGAGTGCGT GACGCCACGGCAACAAG | |
| 169 | MycoPGM2F2899A MID1 | CCATCTCATCCCTGCGTGTCTCCGACTCAG ACGAGTGCGT ACGCCACGGCAACAAG | |

Fragment 2 Reverse Reading Set (Adapter P or Adapter A)

| | | | |
|---|---|---|---|
| 170 | MycoPGM2F2898P | CCTCTCTATGGGCAGTCGGTGAT GACGCCACGGCAACAAG | |
| 171 | MycoPGM2F2899P | CCTCTCTATGGGCAGTCGGTGAT ACGCCACGGCAACAAG | |
| 172 | MycoPGM2R3337A | CCATCTCATCCCTGCGTGTCTCCGACTCAG CAAGTGGTGCAGCTTCAGGATG | |
| 173 | MycoPGM2R3337dA | CCATCTCATCCCTGCGTGTCTCCGACTCAG CARGTGGTGCAGCTTCAKGATG | |
| 174 | MycoPGM2R3169A | CCATCTCATCCCTGCGTGTCTCCGACTCAG GGCGCCGTCGAACAC | |
| 175 | MycoPGM2R3169dA | CCATCTCATCCCTGCGTGTCTCCGACTCAG GGCRCCGTCGAACAC | |

Fragment 3 Forward Reading Set (Adapter A or Adapter P)

| | | | |
|---|---|---|---|
| 176 | MycoPGM2F3148A | CCATCTCATCCCTGCGTGTCTCCGACTCAG CACCCCGGTGTTCGAC | |
| 177 | MycoPGM2R3391P | CCTCTCTATGGGCAGTCGGTGAT CTGGGTGATCATCGAGTACG | |
| 178 | MycoPGM2F3148A MID1 | CCATCTCATCCCTGCGTGTCTCCGACTCAG ACGAGTGCGT CACCCCGGTGTTCGAC | |

TABLE 4-continued

| | | | |
|---|---|---|---|
| | *Mycobacterium* Sequences | | |
| SEQ ID NO: | Name | Sequence | Description |
| | Fragment 3 Reverse Reading Set (Adapter P or Adapter A) | | |
| 179 | MycoPGM2F3148P | CCTCTCTATGGGCAGTCGGTGAT CACCCCGGTGTTCGAC | |
| 180 | MycoPGM2R3391A | CCATCTCATCCCTGCGTGTCTCCGAC<u>TCAG</u> CTGGGTGATCATCGAGTACG | |

TABLE 5

| | | | |
|---|---|---|---|
| | *Streptococcus* Sequences | | |
| SEQ ID NO: | Name | Sequence | Description |
| | *Streptococcus* Fragment 1 | | |
| 181 | StrepF1475a | CCTTGGGACCTGGTGGTT | saliv therm mitisB oralis suis anginosus |
| 182 | StrepF1475b | CCTTAGGACCTGGTGGTT | pyog dysgalac canis equi agalac pneumo sang |
| 183 | StrepF1475c | GCTTTAGGTCCTGGTGGTT | mutans |
| 184 | StrepF1475d | CCTTGGGGCCTGGTGGTT | mitisB |
| 185 | StrepF1475e | CCTTAGGGCCTGGTGGTT | Parasanguinis |
| 186 | StrepR1720a | CTTCTTCGTCGGCAGTCAAC | saliv therm pyog canis |
| 187 | StrepR1720b | CTTCTTCATCAGCAGTCAACC | pyog2 agalac dysgalac |
| 188 | StrepR1720c | CTTCTTCATCAGCAGTTAGC | equi |
| 189 | StrepR1720d | CTTCTTCATCAGCAGTAAGC | mutans |
| 190 | StrepR1720e | CTTCTTCATCAGCTGTCAAC | pneumo |
| 191 | StrepR1720f | CTTCTTCATCGGCTGTCAAC | mitis oralis paras suis |
| 192 | StrepR1720g | CTTCCTCGTCAGCGGTCAAC | sang |
| 193 | StrepR1720h | CTTCTTCGTCCGCTGTCAGC | anginosus |
| 194 | StrepR1720i | CTTCTTCATCCGCTGTTAGC | intermedius |
| | *Streptococcus* Fragment 2 | | |
| 195 | StrepF1875a | TGCGACAGCATGTATTCCTT | |
| 196 | StrepF1875b | CGCAACAGCATGTATTCCTT | agalac |
| 197 | StrepF1875c | TGCAACGGCATGTATTCCTT | pyogenes dysgalac canis |
| 198 | StrepF1875d | GGCAACGGCATGTATTCCTT | intermedius |
| 199 | StrepR2148a | TGAGTTTGAACGACGGAATTT | saliv therm pyog dysgalac pneumo mitisB paras |
| 200 | StrepR2148b | TGAGTTGGAGCGACGGAATTT | canis |
| 201 | StrepR2148c | AGAGTTTGAACGGCGGAATTT | equi anginosus |

TABLE 5-continued

| SEQ ID NO: | Name | Sequence | Description |
|---|---|---|---|
| | *Streptococcus* Sequences | | |
| 202 | StrepR2148d | AGAGTTAGAACGACGGAATTT | mutans |
| 203 | StrepR2148e | TGAGTTTGAACGGCGGAATTT | agalactie |
| 204 | StrepR2148f | TGAGTTAGAACGACGGAATTT | mitis oralis |
| 205 | StrepR2148g | TGAGTTAGAACGGCGGAATTT | sang intermedius |
| | *Streptococcus* Fragment 3 | | |
| 206 | StrepF2885a | TGAACATCGGTCAGGTTATGG | salivarus suis |
| 207 | StrepF2885b | TGAACATTGGTCAGGTTATGG | thermo dysgalac sanguin |
| 208 | StrepF2885c | TGAATATTGGTCAGGTTATGG | pyogenes |
| 209 | StrepF2885d | TGAATATCGGTCAGGTTATGG | pneumo mitis oralis paras |
| 210 | StrepF2885e | TGAACATCGGACAAGTTATGG | canis |
| 211 | StrepF2885f | TGAACATTGGACAGGTTATGG | equi |
| 212 | StrepF2885g | TGAACATTGGGCAAGTTATGG | mutans |
| 213 | StrepF2885h | TGAATATCGGACAAGTTATGG | agalac intermedius |
| 214 | StrepF2885i | TGAATATTGGTCAAGTTATGG | anginosus |
| 215 | StrepR3134a | TGAAGTTTATCATCAACCATGTG | salivarus thermo pyog dysgal canis suis |
| 216 | StrepR3134b | TGCAATTTATCATCAACCATGTG | mutans mitis oralis |
| 217 | StrepR3134c | TGCAACTTATCATCAACCATGTG | agalac |
| 218 | StrepR3134d | TGAAGCTTATCATCTACCATGTG | intermedius |
| 219 | StrepR3134e | TGGAGTTTATCATCTACCATGTG | sang |
| 220 | StrepR3134f | TGAAGCTTATCATCAACCATGTG | equi |
| 221 | StrepR3134g | TGCAATTTATCGTCAACCATGTG | pneumo |
| 222 | StrepR3134h | TGGAGCTTATCATCAACCATGTG | anginosus |
| | *Streptococcus* Fragment 4 | | |
| 223 | StrepF3106a | CTTCACCACATGGTTGATGATAA | saliv thermo pyog mutans paras suis equi |
| 224 | StrepF3106b | CTCCACCACATGGTTGATGATAA | dysgalac canis mitis oralis |
| 225 | StrepF3106c | CTCCACCACATGGTTGACGATAA | pneumo |
| 226 | StrepF3106d | CTCCACCACATGGTAGATGATAA | sang |
| 227 | StrepF3106e | CTTCACCACATGGTAGATGATAA | intermed |
| 228 | StrepR3366a | TTCTGGTACACCTGGTTTTGG | saliv thermo pyog dysgalac paras |
| 229 | StrepR3366b | TTCTGGCACACCTGGTTTTGG | canis sang |
| 230 | StrepR3366c | TTCTGGAACACCTGGTTTTGG | agalac pneumo mitis oralis suis anginosus |
| 231 | StrepR3366d | TTCTGGGACACCTGGTTTTGG | intermed |

TABLE 5-continued

*Streptococcus* Sequences

| SEQ ID NO: | Name | Sequence | Description |
|---|---|---|---|
| 232 | StrepR3366e | TTCTGGTACACCAGGCTTTGG | equi |
| 233 | StrepR3366f | TTCTGGTACCCCTGGTTTTGG | mutans |

PGM Fragment 2 Set (Adapter A, MID or Adapter P)

| | | | |
|---|---|---|---|
| 234 | StrepPGMF1875a MID1 | CCATCTCATCCCTGCGTGTCTCCGACTCAG ACGAGTGCGT | |
| 235 | StrepPGMF1875b MID1 | CCATCTCATCCCTGCGTGTCTCCGACTCAG ACGAGTGCGT | |
| 236 | StrepPGMF1875c MID1 | CCATCTCATCCCTGCGTGTCTCCGACTCAG ACGAGTGCGT | |
| 237 | StrepPGMF1875d MID1 | CCATCTCATCCCTGCGTGTCTCCGACTCAG ACGAGTGCGT | |
| 238 | StrepPGMR2148a | CCTCTCTATGGGCAGTCGGTGAT | |
| 239 | StrepPGMR2148b | CCTCTCTATGGGCAGTCGGTGAT | |
| 240 | StrepPGMR2148c | CCTCTCTATGGGCAGTCGGTGAT | |
| 241 | StrepPGMR2148d | CCTCTCTATGGGCAGTCGGTGAT | |
| 242 | StrepPGMR2148e | CCTCTCTATGGGCAGTCGGTGAT | |
| 243 | StrepPGMR2148f | CCTCTCTATGGGCAGTCGGTGAT | |
| 244 | StrepPGMR2148g | CCTCTCTATGGGCAGTCGGTGAT | |

PGM Fragment 3 Set (Adapter A, MID or Adapter P)

| | | | |
|---|---|---|---|
| 245 | StrepPGMF2885a MID1 | CCATCTCATCCCTGCGTGTCTCCGACTCAG ACGAGTGCGT | |
| 246 | StrepPGMF2885b MID1 | CCATCTCATCCCTGCGTGTCTCCGACTCAG ACGAGTGCGT | |
| 247 | StrepPGMF2885c MID1 | CCATCTCATCCCTGCGTGTCTCCGACTCAG ACGAGTGCGT | |
| 248 | StrepPGMF2885d MID1 | CCATCTCATCCCTGCGTGTCTCCGACTCAG ACGAGTGCGT | |
| 249 | StrepPGMF2885e MID1 | CCATCTCATCCCTGCGTGTCTCCGACTCAG ACGAGTGCGT | |
| 250 | StrepPGMF2885f MID1 | CCATCTCATCCCTGCGTGTCTCCGACTCAG ACGAGTGCGT | |
| 251 | StrepPGMF2885g MID1 | CCATCTCATCCCTGCGTGTCTCCGACTCAG ACGAGTGCGT | |
| 252 | StrepPGMF2885h MID1 | CCATCTCATCCCTGCGTGTCTCCGACTCAG ACGAGTGCGT | |
| 253 | StrepPGMF2885i MID1 | CCATCTCATCCCTGCGTGTCTCCGACTCAG ACGAGTGCGT | |
| 254 | StrepPGMR3134a | CCTCTCTATGGGCAGTCGGTGAT | |
| 255 | StrepPGMR3134b | CCTCTCTATGGGCAGTCGGTGAT | |
| 256 | StrepPGMR3134c | CCTCTCTATGGGCAGTCGGTGAT | |
| 257 | StrepPGMR3134d | CCTCTCTATGGGCAGTCGGTGAT | |
| 258 | StrepPGMR3134e | CCTCTCTATGGGCAGTCGGTGAT | |
| 259 | StrepPGMR3134f | CCTCTCTATGGGCAGTCGGTGAT | |

TABLE 5-continued

Streptococcus Sequences

| SEQ ID NO: | Name | Sequence | Description |
|---|---|---|---|
| 260 | StrepPGMR3134g | CCTCTCTATGGGCAGTCGGTGAT | |
| 261 | StrepPGMR3134h | CCTCTCTATGGGCAGTCGGTGAT | |

PGM Fragment 4 Set (Adapter A, MID or Adapter P)

| SEQ ID NO: | Name | Sequence | Description |
|---|---|---|---|
| 262 | StrepPGMF3106a MID1 | CCATCTCATCCCTGCGTGTCTCCGACTCAG ACGAGTGCGT | |
| 263 | StrepPGMF3106b MID1 | CCATCTCATCCCTGCGTGTCTCCGACTCAG ACGAGTGCGT | |
| 264 | StrepPGMF3106c MID1 | CCATCTCATCCCTGCGTGTCTCCGACTCAG ACGAGTGCGT | |
| 265 | StrepPGMF3106d MID1 | CCATCTCATCCCTGCGTGTCTCCGACTCAG ACGAGTGCGT | |
| 266 | StrepPGMF3106e MID1 | CCATCTCATCCCTGCGTGTCTCCGACTCAG ACGAGTGCGT | |
| 267 | StrepPGMR3366a | CCTCTCTATGGGCAGTCGGTGAT | |
| 268 | StrepPGMR3366b | CCTCTCTATGGGCAGTCGGTGAT | |
| 269 | StrepPGMR3366c | CCTCTCTATGGGCAGTCGGTGAT | |
| 270 | StrepPGMR3366d | CCTCTCTATGGGCAGTCGGTGAT | |
| 271 | StrepPGMR3366e | CCTCTCTATGGGCAGTCGGTGAT | |
| 272 | StrepPGMR3366f | CCTCTCTATGGGCAGTCGGTGAT | |

TABLE 6

Staphylococcus Sequences

| SEQ ID NO: | Name | Sequence | Description |
|---|---|---|---|
| | | Staphylococcus Fragment 1 | |
| 273 | StaphF44a | GAAACTACGCGAGAATTTCAG AAG | aureus, lugdunensis |
| 274 | StaphF44b | GAAATTACGCGAGAATTTCAG AAG | epidermidis, capitis |
| 275 | StaphF44c | GAAATTATGCGAGAATTTCAG AAG | haemolyticus |
| 276 | StaphF44d | GAAACTATGCGAGAATTTCAG AGG | saprophyticus |
| 277 | StaphR278a | CGAAGAGGTGCAGCATAAGTA G | |
| 278 | StaphR278b | CGTAATGGTGCCGCGTATGTT G | intermedius |
| 279 | StaphR278c | CGTAGAGGTGCAGAATACGTT G | saprophyticus |
| 280 | StaphF18a | CCAATATGGAAGACATCGTAA ACG | |

TABLE 6-continued

Staphylococcus Sequences

| SEQ ID NO: | Name | Sequence | Description |
|---|---|---|---|
| | | Staphylococcus Fragment 2 | |
| 281 | StaphF1251a | CCAATTCCGTATCGGTTTATC | |
| 282 | StaphF1251b | CCAATTCCGTATTGGTTTATC | lugdunensis, saprophyticus |
| 283 | StaphR1505a | ACTTCCATTTGAGCACGTTC | |
| 284 | StaphR1505b | ACTTCCATTTGGGCACGTTC | caprae |
| 285 | StaphR1505c | ACTTCCATTTGTGCACGTTC | lugdunensis |
| | | Staphylococcus Fragment 3 | |
| 286 | StaphF1484a | GTGAACGTGCTCAAATGGAAG | |
| 287 | StaphF1484b | GTGAACGTGCCCAAATGGAAG | caprae |
| 288 | StaphF1484c | GTGAACGTGCACAAATGGAAG | lugdunensis |
| 289 | StaphR1715a | ACATAGCTATCTTCTTCATCA GC | |
| 290 | StaphR1715b | ACGTAACTATCCTCTTCATCA GC | epidermidis |
| 291 | StaphR1715c | ACATAGCTATCCTCTTCATCA GC | epidermidis |

TABLE 6-continued

*Staphylococcus* Sequences

| SEQ ID NO: | Name | Sequence | Description |
|---|---|---|---|
| 292 | StaphR1715d | ACATAGCTATCTTCTTCGTCAGC | aureus |
| 293 | StaphR1715e | ACATAACTGTCTTCTTCATCAGC | lugdunensis |

*Staphylococcus* Fragment 4

| | | | |
|---|---|---|---|
| 294 | StaphF3224a | TCGGTGAGATGGAGGTATGG | |
| 295 | StaphF3224b | TCGGTGAGATGGAAGTATGG | lugdunensis |
| 296 | StaphF3224c | TCGGTGAAATGGAAGTATGG | saprophyticus |
| 297 | StaphR3388a | CTCGGAATGATTCTGGAACAC | |
| 298 | StaphR3388b | CTCGGAATGATTCAGGAACAC | intermedius, capitis, lugdunensis, saprophyticus |

TABLE 7

*Burkholderia* Sequences

| SEQ ID NO: | Name | Sequence |
|---|---|---|
| 299 | BUR3 | GAAGAAGCAGTTCGGCAA |
| 300 | BUR4 | GAGTCGATGACGATCAT |
| 301 | recAF1 | CCACGCTCACGCTGCAGG |
| 302 | recAR1 | CGAGCCCGAGCGCACCAG |
| 303 | recAF2 | CGAAGGCGAGATGGGCG |
| 304 | recAR2 | TCGAGACGCACCGACG |
| 305 | recAF3 | GTGCAGGCGAAGATCGTCG |
| 306 | recAR3 | CCATCGCCTCGGCTTCG |

TABLE 8

*Enterococcus* Sequences

| SEQ ID NO: | Name | Sequence |
|---|---|---|
| 307 | tufF1 | GGCGGACGTCACACTCCATTC |
| 308 | tufR1 | CCGTCTTCGATAGCGATTGGGTGG |
| 309 | tufF2 | GGTTGCTCGTGAAGACATCCAAC |
| 310 | tufR2 | CACCAGTAACGTCTGTTGTACGG |
| 311 | tufF3 | CAGGCGATGATGTTCCAGTTATCGC |
| 312 | tufR3 | GTAGCAACAGTACCACGTCCAGTG |

TABLE 9

*Pseudomonas* Sequences

| SEQ ID NO: | Name | Sequence |
|---|---|---|
| 313 | APrU 34 | TGTAAAACGACGGCCAGTGCNGGRTCYTTYTCYTGRCA |
| 314 | M13 (21) 34 | TGTAAAACGACGGCCAGT |
| 315 | UP1E 34 | CAGGAAACAGCTATGACCAYGSNGGNGGNAARTTYRA |
| 316 | M13R 34 | CAGGAAACAGCTATGACC |
| 317 | gyrbF1 | CAGCTGGGACATCCTGGCC |
| 318 | gyrbR1 | TGAGGGATGTTGTTGGTAAAGCAC |
| 319 | gyrbF2 | GTGCTTTACCAACAACATCCCTCA |
| 320 | gyrbR2 | TGTCTTTGGTCTGGGAGCTGAAC |

TABLE 10

IDT Label Sequences

| SEQ ID NO: | Name | Sequence |
|---|---|---|
| 321 | Br2-F-MID2 | CCATCTCATCCCTGCGTGTCTCCGACTCAGACGCTCGACAAGYGGCGIACGGGTGAGTAA |
| 322 | Br2-F-MID3 | CCATCTCATCCCTGCGTGTCTCCGACTCAGAGACGCACTCAGYGGCGIACGGGTGAGTAA |
| 323 | Br2-F-MID4 | CCATCTCATCCCTGCGTGTCTCCGACTCAGAGCACTGTAGAGYGGCGIACGGGTGAGTAA |
| 324 | Br2-F-MID5 | CCATCTCATCCCTGCGTGTCTCCGACTCAGATCAGACACGAGYGGCGIACGGGTGAGTAA |
| 325 | Br2-F-MID6 | CCATCTCATCCCTGCGTGTCTCCGACTCAGATATCGCGAGAGYGGCGIACGGGTGAGTAA |
| 326 | Br2-F-MID7 | CCATCTCATCCCTGCGTGTCTCCGACTCAGCGTGTCTCTAAGYGGCGIACGGGTGAGTAA |
| 327 | Br2-F-MID8 | CCATCTCATCCCTGCGTGTCTCCGACTCAGCTCGCGTGTCAGYGGCGIACGGGTGAGTAA |
| 328 | Br3-F-MID2 | CCATCTCATCCCTGCGTGTCTCCGACTCAGACGCTCGACAACTCCTACGGGAGGCAGCAG |
| 329 | Br3-F-MID3 | CCATCTCATCCCTGCGTGTCTCCGACTCAGAGACGCACTCACTCCTACGGGAGGCAGCAG |
| 330 | Br3-F-MID4 | CCATCTCATCCCTGCGTGTCTCCGACTCAGAGCACTGTAGACTCCTACGGGAGGCAGCAG |
| 331 | Br3-F-MID5 | CCATCTCATCCCTGCGTGTCTCCGACTCAGATCAGACACGACTCCTACGGGAGGCAGCAG |
| 332 | Br3-F-MID6 | CCATCTCATCCCTGCGTGTCTCCGACTCAGATATCGCGAGACTCCTACGGGAGGCAGCAG |
| 333 | Br3-F-MID7 | CCATCTCATCCCTGCGTGTCTCCGACTCAGCGTGTCTCTAACTCCTACGGGAGGCAGCAG |
| 334 | Br3-F-MID8 | CCATCTCATCCCTGCGTGTCTCCGACTCAGACGAGTGCGTACTCCTACGGGAGGCAGCAG |

The following examples serve to illustrate the present invention. The examples are in no way intended to limit the scope of the invention.

Example 1: Direct Detection Using Primers with
Adapter Sequence and Target Specific Sequence A biological sample is obtained from a human individual
and nucleic acid extracted using the MagNA Pure LC
instrument (Roche Molecular Diagnostics, Germany). A
post-extraction step is performed to remove human nucleic
acid from the sample.

The remaining nucleic acid from the sample is amplified
using universal 16S rDNA and ITS rDNA primers. The
amplification is performed using PCR. The resulting ampli-
fied nucleic acid is then amplified again using PCR with
bacterial or fungal specific DNA oligonucleotide primer
pairs.

Next, primer pairs comprising both a target specific
sequence (e.g., specific for a particular sequence within a
microbial gene) and an adapter sequence are used to perform
a third amplification process. The forward and reverse
primers in the primer pairs contain different adapter
sequences. The primers can optionally include a MID. This
process attaches the adapter sequences to the microbial
nucleic acid.

The amplicons are then sequenced using a high through-
put, massively parallel platform to identify the nucleic acid
sequence of the microbial agent(s) in the sample. The
sequences are compared against a BLAST of the rDNA
targets to identify the specific microbial agent(s) present in
the sample.

Example 2: Direct Detection Using Primers with
Adapter Sequence and Multiplex Identifier A biological sample is obtained from a human individual
and nucleic acid extracted using the MagNA Pure LC
instrument (Roche Molecular Diagnostics, Germany). A
post-extraction step is performed to remove human nucleic
acid from the sample.

The remaining nucleic acid from the sample is amplified
using universal 16S rDNA and ITS rDNA primers. The
amplification is performed using PCR. The resulting ampli-
fied nucleic acid is then amplified again using PCR with
bacterial or fungal specific DNA oligonucleotide primer
pairs comprising a target specific sequence and a tag.

Next, primer pairs comprising an adapter sequence and a
MID are used to perform a third amplification process, in
which the MID hybridizes to the tag from the second
amplification process. The forward and reverse primers in
the primer pairs contain different adapter sequences. This
process attaches the adapter sequence to the microbial
nucleic acid.

The amplicons are then sequenced using a high through-
put, massively parallel platform to identify the nucleic acid
sequence of the microbial agent(s) in the sample. The
sequences are compared against a BLAST of the rDNA
targets to identify the specific microbial agent(s) present in
the sample.

Alternatively, bi-directional sequencing can be per-
formed, in which the forward and reverse primers in each
primer pair have the opposite adapter sequence attached
thereto.

Example 3: Direct Detection Using Enzyme
Ligation to Attach Adapter

A biological sample is obtained from a human individual
and nucleic acid extracted using the MagNA Pure LC instrument (Roche Molecular Diagnostics, Germany). A
post-extraction step is performed to remove human nucleic
acid from the sample.

The remaining nucleic acid from the sample is amplified
using universal 16S rDNA and ITS rDNA primers. The
amplification is performed using PCR. The resulting ampli-
fied nucleic acid is then amplified again using PCR with
bacterial or fungal specific DNA oligonucleotide primer
pairs.

Next, enzyme ligation is performed to attached a nucleo-
tide comprising an adapter sequence and MID to the micro-
bial nucleic acid. The resulting adapter-tagged microbial
nucleic acid is then amplified using a primer pair to produce
amplicons.

The amplicons are then sequenced using a high through-
put, massively parallel platform to identify the nucleic acid
sequence of the microbial agent(s) in the sample. The
sequences are compared against a BLAST of the rDNA
targets to identify the specific microbial agent(s) present in
the sample.

Example 4: Direct Identification of Different
Microbial Species in Polymicrobial Samples A ~459 bp segment of the V3-V4 bacterial 16s rrna gene
was amplified with target-specific PCR primers with 5'
overhang adapters. The amplification mix contained the
following ingredients in sufficient volume for a quarter plate
and a half plate.

| Reagents | x1 (uL) | x30 (uL) | x60 (uL) |
|---|---|---|---|
| 16Sv3v4-F Primer (1 uM) | 5 | 150 | 300 |
| 16Sv3v4-R Primer (1 uM) | 5 | 150 | 300 |
| 2X KAPA HiFi HotStart Ready Mix | 12.5 | 375 | 750 |
| Total | 22.5 | 675 | 1,350 |

Index sequences and adapters were ligated to the 5' and 3'
ends of the amplicons to allow for paired end sequencing.
The library derived from 15 samples was normalized and
pooled, and loaded onto a MiSeq® sequencer for clustering
and paired-end sequencing with the 250 bp paired end
sequencing chemistry and a nano-flow cell.

Paired-end reads were merged and quality-filtered.
Sequences were dereplicated, singletons were discarded,
and then sequences clustered into centroids with a radius of
2%. Operational taxonomic units (OTUs) constructed from
the centroids for each sample were searched against the
Living Tree Program database release 111, available at
http://www.arb-silva.de/projects/living-tree/ and/or the
NCBI 16S rrna sequence database. Species identifications
and the relative abundance of each identified species in the
samples tested were tabulated.
Results
Sequence Metrics
421,105 raw reads were obtained, 368,337 reads passed
the quality filtering stage for a PF rate of 87.5%. 93% of
reads had a median Q value >Q30. The read distribution was
normally distributed between the 15 samples in the pooled
library with 4.1%±1.9% (1 SD) reads per sample. The
negative control did not have an appreciable number of
detectable reads (Table 11).
The vast majority of merged paired end reads produced
full length amplicon sequence of 465 bp, or 427 bp after the
target-specific PCR primers were trimmed.

TABLE 11

| | | % of PF reads | reads clustered in OTUs | OTUs (>0.5%) |
|---|---|---|---|---|
| Sample | Description | | | |
| M1 | mixed organisms | 4.37 | 13681 | 7 |
| M2 | mixed organisms | 4.05 | 11764 | 14 |
| M3 | mixed organisms | 6.71 | 19967 | 8 |
| M4 | mixed organisms | 3.65 | 10087 | 11 |
| M5 | mixed organisms | 7.77 | 19821 | 8 |
| M6 | mixed organisms | 3.30 | 7232 | 6 |
| S1 | pure sample | 5.55 | 19673 | 1 |
| S2 | pure sample | 2.51 | 8874 | 1 |
| S3 | pure sample | 4.39 | 15577 | 2 |

*Reads and Operational Taxonomies Units (OTUs) per Sample*

TABLE 11-continued

| | | % of PF reads | reads clustered in OTUs | OTUs (>0.5%) |
|---|---|---|---|---|
| Sample | Description | | | |
| S4 | pure sample | 2.27 | 8073 | 1 |
| S5 | pure sample | 6.78 | 23824 | 1 |
| S6 | pure sample | 3.05 | 10899 | 1 |
| P1 | patient sample | 2.78 | 9731 | 1 |
| P2 | patient sample | 1.46 | 5147 | 1 |
| P3 | patient sample | 2.21 | 7705 | 1 |
| NEG | Negative ctrl | 0.007 | NA | NA |

*Reads and Operational Taxonomies Units (OTUs) per Sample*

Organism Identification is shown in Table 12 below:

TABLE 12

*Identification of Pure (S1-S6) and Patient (P1-P3) Samples*

| Sample | Identification | Align (bp) | Match | % of Reads | Reads (N) | Experimental Input |
|---|---|---|---|---|---|---|
| P1_S13 | *Pseudomonas_aeruginosa* | 425 | 100% | 100% | 9731 | *Pseudomonas aeruginosa* |
| P2_S14 | *Neisseria_sicca* | 425 | 99.5% | 100% | 5147 | *Neisseria sicca* |
| P3_S15 | *Bacillus_cereus* | 425 | 100% | 100% | 7705 | *Bacillus cereus* |
| S1_S7 | *Neisseria_lactamica* | 425 | 100% | 100% | 19673 | *Neisseria lactamica* |
| S2_S8 | *Acinetobacter_baumannii* | 425 | 100% | 100% | 8874 | *Acinetobacter baumannii* |
| S3_S9 | *Salmonella_enterica* | 425 | 100% | 69.0% | 10753 | *Salmonella cholereasuis* |
| S3_S9 | *Enterobacter_cloacae* | 425 | 99.5% | 31.0% | 4824 | |
| S4_S10 | *E. fergusonii/E. coli/Shigella* | 425 | 100% | 100% | 8073 | *Shigella sonnei* |
| S5_S11 | *Bordetella_parapertussis* | 425 | 100% | 100% | 23824 | *Bordetella parapertussis* |
| S6_S12 | *E. fergusonii/E. coli/Shigella* | 425 | 100% | 100% | 10899 | *E. coli* |

The bioinformatic pipeline successfully identified the input species in the 6 pure samples and 3 patient samples (Table 12). Sample 3 appeared to contain a mixture of two species at a 2:1 ratio. The origin of the second species (*E. cloacae*) is not known.

Table 13 below demonstrates successful recovery of most input species from the mixed samples. *E. cloacae*, used in samples M1 and M2, appeared as a contaminant in samples M3 and M5.

TABLE 13

*Identification of Six Mixed Bacterial Samples*

| Sample | OTUId | Reads | Pct | Identity | Input | |
|---|---|---|---|---|---|---|
| M1_S1 | OTU_1 | 5580 | 40.8% | *Acinetobacter_baumannii* | *Acinetobacter baumannii* | |
| M1_S1 | OTU_2 | 2480 | 18.1% | *E. fergusonii/E. coli/Shigella* | *Escherichia coli* | *Shigella sonnei* |
| M1_S1 | OTU_3 | 2047 | 15.0% | *Enterobacter_aerogenes* | *Enterobacter aerogenes* | |
| M1_S1 | OTU_5 | 1614 | 11.8% | *Enterobacter_cloacae* | *Enterobacter cloacae* | |
| M1_S1 | OTU_4 | 861 | 6.3% | *Bordetella_pertussis* | *Bordetella pertussis* | |
| M1_S1 | OTU_6 | 573 | 4.2% | *Salmonella_enterica* | *Salmonella choleraesuis* | |
| M1_S1 | OTU_7 | 518 | 3.8% | *Klebsiella_variicola* | *Klebsiella pneumoniae* *Nocardia farcinica* | |
| M2_S2 | OTU_1 | 3984 | 33.9% | *Staphylococcus_epidermidis/capitis* | *Staphylococcus epidermidis* | *Staphylococcus aureus* |
| M2_S2 | OTU_15 | 1121 | 9.5% | *Staphylococcus_saprophyticus* | *Staphylococcus saprophyticus* | |
| M2_S2 | OTU_3 | 1058 | 9.0% | *Streptococcus_pyogenes* | *Strep pyogenes* group a | |
| M2_S2 | OTU_2 | 1032 | 8.8% | *Acinetobacter_baumannii* | *Acinetobacter baumannii* | |
| M2_S2 | OTU_5 | 934 | 7.9% | *E. fergusonii/E. coli/Shigella* | *Shigella sonnei* | *Escherichia coli* |
| M2_S2 | OTU_6 | 807 | 6.9% | *Streptococcus_agalactiae* | *Strep agalactiae* group b | |
| M2_S2 | OTU_4 | 742 | 6.3% | *Neisseria_lactamica* | *Neisseria lactamica* | |
| M2_S2 | OTU_7 | 574 | 4.9% | *Proteus_mirabilis* | *Proteus mirabilis* | |
| M2_S2 | OTU_8 | 416 | 3.5% | *Enterobacter_aerogenes* | *Enterobacter aerogenes* | |
| M2_S2 | OTU_9 | 296 | 2.5% | *Enterobacter_cloacae* | *Enterobacter cloacae* | |
| M2_S2 | OTU 11 | 274 | 2.3% | *Haemophilus_aegyptius* | *Haemophilus influenzae* | |
| M2_S2 | OTU_12 | 179 | 1.5% | *Bordetella_pertussis* | *Bordetella parapertussis* | *Bordetella pertussis* |
| M2_S2 | OTU_10 | 166 | 1.4% | *Pseudomonas_aeruginosa* | *Pseudomonas aeruginosa* | |
| M2_S2 | OTU_13 | 108 | 0.9% | *0.9%:Salmonella_enterica* | *Salmonella choleraesuis* | |
| M2_S2 | OTU_14 | 73 | 0.6% | *Klebsiella_variicola* | *Klebsiella pneumoniae* *Ochrobactrum anthropi* *Camphylobacter jejuni* | |

TABLE 13-continued

Identification of Six Mixed Bacterial Samples

| Sample | OTUId | Reads | Pct | Identity | Input | |
|---|---|---|---|---|---|---|
| M3_S3 | OTU_1 | 7103 | 35.6% | *Staphylococcus_capitis* | *Staphylococcus aureus* | |
| | OTU_6 | 4117 | 20.6% | *Staphylococcus_saprophyticus* | *Staphylococcus saprophyticus* | |
| | OTU_2 | 3380 | 16.9% | *Proteus_mirabilis* | *Proteus mirabilis* | |
| | OTU_3 | 2082 | 10.4% | *Streptococcus_agalactiae* | *Strep agalactiae* group b | |
| | OTU_4 | 1396 | 7.0% | *E. fergusonii/E. coli/Shigella* | *Escherichia coli* | |
| | OTU_5 | 1046 | 5.2% | *Pseudomonas_aeruginosa* | *Pseudomonas aeruginosa* | |
| | OTU_7 | 574 | 2.9% | *Salmonella_enterica* | *Salmonella choleraesuis* | |
| | OTU_8 | 269 | 1.3% | *Enterobacter_cloacae* | | |
| M4_S4 | OTU_1 | 3999 | 39.6% | *Staphylococcus_epidermidis/capitis* | *Staphylococcus epidermidis* | |
| M4_S4 | OTU_2 | 1677 | 16.6% | *Streptococcus_pyogenes* | *Strep pyogenes* group a | |
| M4_S4 | OTU_3 | 1215 | 12.0% | *Acinetobacter_baumannii* | *Acinetobacter baumannii* | |
| M4_S4 | OTU_4 | 1069 | 10.6% | *Neisseria_lactamica* | *Neisseria lactamica* | |
| M4_S4 | OTU_5 | 533 | 5.3% | *Enterobacter_aerogenes* | *Enterobacter aerogenes* | |
| M4_S4 | OTU_6 | 490 | 4.9% | *Haemophilus_aegyptius* | *Haemophilus influenzae* | |
| M4_S4 | OTU_7 | 369 | 3.7% | *Enterobacter_cloacae* | *Enterobacter cloacae* | |
| M4_S4 | OTU_8 | 240 | 2.4% | *Bordetella_pertussis* | *Bordetella parapertussis* | *Bordetella pertussis* |
| M4_S4 | OTU_10 | 222 | 2.2% | *E. fergusonii/E. coli/Shigella* | *Shigella sonnei* | |
| M4_S4 | OTU_9 | 137 | 1.4% | *Salmonella_enterica* | *Salmonella choleraesuis* | |
| M4_S4 | OTU_11 | 132 | 1.3% | *Klebsiella_variicola* | *Klebsiella pneumoniae* | |
| | | | | | *Nocardia farcinica* | |
| | | | | | *Ochrobactrum anthropi* | |
| | | | | | *Camphylobacter jejuni* | |
| M5_S5 | OTU_1 | 6110 | 437.7% | *Streptococcus_pyogenes* | *Strep pyogenes* group a | |
| M5_S5 | OTU_2 | 4336 | 310.6% | *Acinetobacter_baumannii* | *Acinetobacter baumannii* | |
| M5_S5 | OTU_3 | 3311 | 237.2% | *Neisseria_lactamica* | *Neisseria lactamica* | |
| M5_S5 | OTU_4 | 3151 | 225.7% | *Proteus_mirabilis* | *Proteus mirabilis* | |
| M5_S5 | OTU_5 | 1526 | 109.3% | *Haemophilus_aegyptius* | *Haemophilus influenzae* | |
| M5_S5 | OTU_6 | 720 | 51.6% | *E. fergusonii/E. coli/Shigella* | *Shigella sonnei* | |
| M5_S5 | OTU_7 | 453 | 32.4% | *Salmonella_enterica* | *Salmonella choleraesuis* | |
| M5_S5 | OTU_8 | 207 | 14.8% | *Enterobacter_cloacae* | | |
| | | | | | *Nocardia farcinica* | |
| | | | | | *Corynebacterium* | |
| M6_S6 | OTU_3 | 1697 | 23.5% | *Enterobacter_aerogenes* | *Enterobacter aerogenes* | |
| M6_S6 | OTU_4 | 1546 | 21.4% | *Bordetella_pertussis* | *Bordetella pertussis* | *Bordetella parapertussis* |
| M6_S6 | OTU_5 | 1206 | 16.7% | *Enterobacter_cloacae* | *Enterobacter cloacae* | |
| M6_S6 | OTU_2 | 1204 | 16.6% | *E. fergusonii/E. coli/Shigella* | *Escherichia coli* | |
| M6_S6 | OTU_1 | 1131 | 15.6% | *Pseudomonas_aeruginosa* | *Pseudomonas aeruginosa* | |
| M6_S6 | OTU_6 | 448 | 6.2% | *Klebsiella_variicola* | *Klebsiella pneumoniae* | |
| | | | | | *Camphylobacter jejuni* | |

These results demonstrate that the methods of the present application, which generate high quality paired-end sequence reads for sequence fragments of short length (in this case a 427 bp was used), accurately identify bacterial species in polymicrobial samples through rDNA amplification and sequencing.

Example 5: Direct Identification of Different Microbial Species in Polymicrobial Samples from Subjects Affected by Infections Difficult to Diagnose Biological fluids, including urine, sputum, vaginal fluid, sperm, blood and synovial fluid are collected from subjects affected by infections that are difficult to diagnose. The subjects are affected by chronic wound infections, lung infections, urinary tract infections, vaginal infections or infections of otherwise sterile body sites or of prosthetic implants. The samples are directly analyzed for the presence of gram-positive and gram-negative bacterial species without the need for culturing the bacterial colonies.

Results

Organisms that constitute 10% or more of a mixed population of three or more bacterial species that are present in the fluid sample are detected by 16s rDNA as described in Example 4 above.

That which is claimed is:

1. A kit for determining the presence of a plurality of microbial agents in a polymicrobial sample without culturing the microbial agents, comprising an amplification reaction mixture containing a plurality of oligonucleotide primers selected from the group consisting of SEQ ID NOS: 89-335, wherein the amplification reaction mixture comprises a primer pair that amplifies at least one target sequence of bacterial 16S rDNA, at least one target sequence of fungal ITS rDNA, and at least one target sequence of each of *Mycobacterium* rpoB, *Staphylococcus* rpoB, *Streptococcus* rpoB, *Burkholderia* recA, *Enterococcus* tuf, and *Pseudomonas* gvrB, wherein:

the primer pair that amplifies at least one target sequence of bacterial 16S rDNA comprises a forward primer and a reverse primer selected from SEQ ID NOs: 89-118;

the primer pair that amplifies at least one target sequence of fungal ITS rDNA comprises a forward primer and a reverse primer selected from SEQ ID NOs: 119-128;

the primer pair that amplifies at least one target sequence of *Mycobacterium* rpoB comprises a forward primer and a reverse primer selected from SEQ ID NOs: 139-152;

the primer pair that amplifies at least one target sequence of *Streptococcus* rpoB comprises forward primer and reverse primer selected from SEQ ID NOs: 181-233;

the primer pair that amplifies at least one target sequence of *Staphylococcus* rpoB comprises forward primer and reverse primer selected from SEQ ID NOs: 273-298;

the primer pair that amplifies at least one target sequence of *Burkholderia* recA comprises forward primer and reverse primer selected from SEQ ID NOs: 299-306;

the primer pair that amplifies at least one target sequence of *Enterococcus* tuf comprises forward primer and reverse primer selected from SEQ ID NOs: 307-312;

the primer pair that amplifies at least one target sequence of *Pseudomonas* gvrB comprises forward primer and reverse primer selected from SEQ ID NOS: 313-320; and wherein one or more of the oligonucleotide primers comprises an adapter sequence, wherein the adapter sequence is selected from the group consisting of SEQ ID NO: 1 and SEQ ID NO: 2.

2. The kit of claim 1, wherein the primers further comprise a multiplex identifier sequence.

3. The kit of claim 2, wherein the primers further comprise a tag sequence selected from the group consisting of SEQ ID NO:3 and SEQ ID NO:4.

4. A kit comprising an amplification reaction mixture for amplifying a plurality of microbial target sequences in a polymicrobial sample without culturing the polymicrobial sample, wherein the amplification reaction mixture comprises primers that specifically amplify at least one target sequence of bacterial 16S rDNA, at least one target sequence of fungal ITS rDNA, and at least one target sequence of each of *Mycobacterium* rpoB, *Staphylococcus* rpoB, *Streptococcus* rpoB, *Burkholderia* recA, *Enterococcus* tuf, and *Pseudomonas* gvrB, wherein:

the primers that specifically amplify at least one target sequence of bacterial 16S rDNA comprise a forward primer selected from among SEQ ID NOs: 89-95, 98-102, 104-110, or 113-117 and a reverse primer selected from among SEQ ID NOs: 96, 97, 103, 111, 112, or 118;

the primers that specifically amplify at least one target sequence of fungal ITS rDNA comprise a forward primer selected from among SEQ ID NOs: 119, 121, 123, 125, 127, 129, 131, 133, 135, 137, 335, or 337 and a reverse primer selected from among SEQ ID NOs: 120, 122, 124, 126, 128, 130, 132, 134, 136, 138, 336, or 338;

the primers that specifically amplify at least one target sequence of *Mycobacterium* rpoB comprise a forward primer selected from among SEQ ID NOs: 139, 141, 143, 144, 151, 153, 155, 157, 158, 160, 162, 163, 168, 169, 170, 171, 176, 178, or 179 and a reverse primer selected from among SEQ ID NOs: 140, 142, 145-150, 152, 154, 156, 159, 161, 164-167, 172-175, 177, or 180;

the primers that specifically amplify at least one target sequence of *Streptococcus* rpoB comprise a forward primer selected from among SEQ ID NOs: 181-185, 195-198, 206-214, 223-227, 234-237, 245-253, or 262-266, and a reverse primer selected from among SEQ ID NOS: 186-194, 199-205, 215-222, 228-233, 238-244, 254-261, or 267-272;

the primers that specifically amplify at least one target sequence of *Staphylococcus* rpoB comprise a forward primer selected from among SEQ ID NOs: 273-276, 280-282, 286-288, 294-296 and a reverse primer selected from among SEQ ID NOs: 277-279, 283-285, 289-293, 297-298;

the primers that specifically amplify at least one target sequence of *Burkholderia* recA comprise a forward primer having SEQ ID NOs: 299, 301, 303, or 305, and a reverse primer having SEQ ID NOs: 300, 302, 304, or 306;

the primers that specifically amplify at least one target sequence of *Enterococcus* tuf comprise a forward primer having SEQ ID NOs: 307, 309, or 311, and a reverse primer having SEQ ID NOS: 308, 310, or 312;

the primers that specifically amplify at least one target sequence of *Pseudomonas* gvrB comprise a forward primer having SEQ ID NOs: 317 or 319, and a reverse primer having SEQ ID NOS: 318 or 320; and wherein one or more of the oligonucleotide primers comprises an adapter sequence, wherein the adapter sequence is selected from the group consisting of SEQ ID NO: 1 and SEQ ID NO: 2.

5. The kit of claim 4, wherein the primers further comprise a multiplex identifier sequence.

6. The kit of claim 5, wherein the primers further comprise a tag sequence selected from the group consisting of SEQ ID NO:3 and SEQ ID NO:4.

\* \* \* \* \*

```
                        SEQUENCE LISTING

Sequence total quantity: 338
SEQ ID NO: 1              moltype = DNA   length = 30
FEATURE                   Location/Qualifiers
misc_feature              1..30
                          note = Description of Artificial Sequence: Syntheticprimer
source                    1..30
                          mol_type = other DNA
                          organism = synthetic construct
SEQUENCE: 1
ccatctcatc cctgcgtgtc tccgactcag                                      30

SEQ ID NO: 2              moltype = DNA   length = 23
```

-continued

```
FEATURE              Location/Qualifiers
misc_feature         1..23
                     note = Description of Artificial Sequence: Syntheticprimer
source               1..23
                     mol_type = other DNA
                     organism = synthetic construct
SEQUENCE: 2
cctctctatg ggcagtcggt gat                                          23

SEQ ID NO: 3         moltype = DNA  length = 22
FEATURE              Location/Qualifiers
misc_feature         1..22
                     note = Description of Artificial Sequence: Syntheticprimer
source               1..22
                     mol_type = other DNA
                     organism = synthetic construct
SEQUENCE: 3
acactgacga catggttcta ca                                           22

SEQ ID NO: 4         moltype = DNA  length = 22
FEATURE              Location/Qualifiers
misc_feature         1..22
                     note = Description of Artificial Sequence: Syntheticprimer
source               1..22
                     mol_type = other DNA
                     organism = synthetic construct
SEQUENCE: 4
tacggtagca gagacttggt ct                                           22

SEQ ID NO: 5         moltype = DNA  length = 10
FEATURE              Location/Qualifiers
misc_feature         1..10
                     note = Description of Artificial Sequence: Syntheticprimer
source               1..10
                     mol_type = other DNA
                     organism = synthetic construct
SEQUENCE: 5
acgagtgcgt                                                         10

SEQ ID NO: 6         moltype = DNA  length = 10
FEATURE              Location/Qualifiers
misc_feature         1..10
                     note = Description of Artificial Sequence: Syntheticprimer
source               1..10
                     mol_type = other DNA
                     organism = synthetic construct
SEQUENCE: 6
acgctcgaca                                                         10

SEQ ID NO: 7         moltype = DNA  length = 10
FEATURE              Location/Qualifiers
misc_feature         1..10
                     note = Description of Artificial Sequence: Syntheticprimer
source               1..10
                     mol_type = other DNA
                     organism = synthetic construct
SEQUENCE: 7
agacgcactc                                                         10

SEQ ID NO: 8         moltype = DNA  length = 10
FEATURE              Location/Qualifiers
misc_feature         1..10
                     note = Description of Artificial Sequence: Syntheticprimer
source               1..10
                     mol_type = other DNA
                     organism = synthetic construct
SEQUENCE: 8
agcactgtag                                                         10

SEQ ID NO: 9         moltype = DNA  length = 10
FEATURE              Location/Qualifiers
misc_feature         1..10
                     note = Description of Artificial Sequence: Syntheticprimer
source               1..10
                     mol_type = other DNA
                     organism = synthetic construct
SEQUENCE: 9
atcagacacg                                                         10
```

```
SEQ ID NO: 10          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct SEQUENCE: 10
atatcgcgag                                                                  10

SEQ ID NO: 11          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct SEQUENCE: 11
cgtgtctcta                                                                  10

SEQ ID NO: 12          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct SEQUENCE: 12
ctcgcgtgtc                                                                  10

SEQ ID NO: 13          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct SEQUENCE: 13
tagtatcagc                                                                  10

SEQ ID NO: 14          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct SEQUENCE: 14
tctctatgcg                                                                  10

SEQ ID NO: 15          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct SEQUENCE: 15
tgatacgtct                                                                  10

SEQ ID NO: 16          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct SEQUENCE: 16
tactgagcta                                                                  10

SEQ ID NO: 17          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct SEQUENCE: 17
catagtagtg                                                                  10
```

```
SEQ ID NO: 18          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct
SEQUENCE: 18
cgagagatac                                                            10

SEQ ID NO: 19          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct
SEQUENCE: 19
atacgacgta                                                            10

SEQ ID NO: 20          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct
SEQUENCE: 20
tcacgtacta                                                            10

SEQ ID NO: 21          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct
SEQUENCE: 21
cgtctagtac                                                            10

SEQ ID NO: 22          moltype = DNA   length = 10
FEATURE                Location/Qualifiers
misc_feature           1..10
                       note = Description of Artificial Sequence: Syntheticprimer
source                 1..10
                       mol_type = other DNA
                       organism = synthetic construct
SEQUENCE: 22
tctacgtagc                                                            10

SEQ ID NO: 23          moltype = DNA   length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 23
ccatctcatc cctgcgtgtc tccgactcag acgagtgcgt                           40

SEQ ID NO: 24          moltype = DNA   length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 24
ccatctcatc cctgcgtgtc tccgactcag acgctcgaca                           40

SEQ ID NO: 25          moltype = DNA   length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 25
```

-continued

```
ccatctcatc cctgcgtgtc tccgactcag agacgcactc                         40

SEQ ID NO: 26          moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 26
ccatctcatc cctgcgtgtc tccgactcag agcactgtag                         40

SEQ ID NO: 27          moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 27
ccatctcatc cctgcgtgtc tccgactcag atcagacacg                         40

SEQ ID NO: 28          moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 28
ccatctcatc cctgcgtgtc tccgactcag atatcgcgag                         40

SEQ ID NO: 29          moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 29
ccatctcatc cctgcgtgtc tccgactcag cgtgtctcta                         40

SEQ ID NO: 30          moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 30
ccatctcatc cctgcgtgtc tccgactcag ctcgcgtgtc                         40

SEQ ID NO: 31          moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 31
ccatctcatc cctgcgtgtc tccgactcag tagtatcagc                         40

SEQ ID NO: 32          moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 32
ccatctcatc cctgcgtgtc tccgactcag tctctatgcg                         40

SEQ ID NO: 33          moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
```

-continued

```
SEQUENCE: 33
ccatctcatc cctgcgtgtc tccgactcag tgatacgtct                          40

SEQ ID NO: 34        moltype = DNA   length = 40
FEATURE              Location/Qualifiers
misc_feature         1..40
                     note = Description of Artificial Sequence: Syntheticprimer
source               1..40
                     mol_type = other DNA
                     organism = synthetic construct
SEQUENCE: 34
ccatctcatc cctgcgtgtc tccgactcag tactgagcta                          40

SEQ ID NO: 35        moltype = DNA   length = 40
FEATURE              Location/Qualifiers
misc_feature         1..40
                     note = Description of Artificial Sequence: Syntheticprimer
source               1..40
                     mol_type = other DNA
                     organism = synthetic construct
SEQUENCE: 35
ccatctcatc cctgcgtgtc tccgactcag catagtagtg                          40

SEQ ID NO: 36        moltype = DNA   length = 40
FEATURE              Location/Qualifiers
misc_feature         1..40
                     note = Description of Artificial Sequence: Syntheticprimer
source               1..40
                     mol_type = other DNA
                     organism = synthetic construct
SEQUENCE: 36
ccatctcatc cctgcgtgtc tccgactcag cgagagatac                          40

SEQ ID NO: 37        moltype = DNA   length = 40
FEATURE              Location/Qualifiers
misc_feature         1..40
                     note = Description of Artificial Sequence: Syntheticprimer
source               1..40
                     mol_type = other DNA
                     organism = synthetic construct
SEQUENCE: 37
ccatctcatc cctgcgtgtc tccgactcag atacgacgta                          40

SEQ ID NO: 38        moltype = DNA   length = 40
FEATURE              Location/Qualifiers
misc_feature         1..40
                     note = Description of Artificial Sequence: Syntheticprimer
source               1..40
                     mol_type = other DNA
                     organism = synthetic construct
SEQUENCE: 38
ccatctcatc cctgcgtgtc tccgactcag tcacgtacta                          40

SEQ ID NO: 39        moltype = DNA   length = 40
FEATURE              Location/Qualifiers
misc_feature         1..40
                     note = Description of Artificial Sequence: Syntheticprimer
source               1..40
                     mol_type = other DNA
                     organism = synthetic construct
SEQUENCE: 39
acgcactcgt ctgagtcgga gacacgcagg gatgagatgg                          40

SEQ ID NO: 40        moltype = DNA   length = 40
FEATURE              Location/Qualifiers
misc_feature         1..40
                     note = Description of Artificial Sequence: Syntheticprimer
source               1..40
                     mol_type = other DNA
                     organism = synthetic construct
SEQUENCE: 40
tgtcgagcgt ctgagtcgga gacacgcagg gatgagatgg                          40

SEQ ID NO: 41        moltype = DNA   length = 40
FEATURE              Location/Qualifiers
misc_feature         1..40
                     note = Description of Artificial Sequence: Syntheticprimer
source               1..40
                     mol_type = other DNA
```

-continued

```
                             organism = synthetic construct
SEQUENCE: 41
gagtgcgtct ctgagtcgga gacacgcagg gatgagatgg                              40

SEQ ID NO: 42              moltype = DNA  length = 40
FEATURE                    Location/Qualifiers
misc_feature               1..40
                           note = Description of Artificial Sequence: Syntheticprimer
source                     1..40
                           mol_type = other DNA
                           organism = synthetic construct
SEQUENCE: 42
ctacagtgct ctgagtcgga gacacgcagg gatgagatgg                              40

SEQ ID NO: 43              moltype = DNA  length = 40
FEATURE                    Location/Qualifiers
misc_feature               1..40
                           note = Description of Artificial Sequence: Syntheticprimer
source                     1..40
                           mol_type = other DNA
                           organism = synthetic construct
SEQUENCE: 43
cgtgtctgat ctgagtcgga gacacgcagg gatgagatgg                              40

SEQ ID NO: 44              moltype = DNA  length = 40
FEATURE                    Location/Qualifiers
misc_feature               1..40
                           note = Description of Artificial Sequence: Syntheticprimer
source                     1..40
                           mol_type = other DNA
                           organism = synthetic construct
SEQUENCE: 44
ctcgcgatat ctgagtcgga gacacgcagg gatgagatgg                              40

SEQ ID NO: 45              moltype = DNA  length = 40
FEATURE                    Location/Qualifiers
misc_feature               1..40
                           note = Description of Artificial Sequence: Syntheticprimer
source                     1..40
                           mol_type = other DNA
                           organism = synthetic construct
SEQUENCE: 45
tagagacacg ctgagtcgga gacacgcagg gatgagatgg                              40

SEQ ID NO: 46              moltype = DNA  length = 40
FEATURE                    Location/Qualifiers
misc_feature               1..40
                           note = Description of Artificial Sequence: Syntheticprimer
source                     1..40
                           mol_type = other DNA
                           organism = synthetic construct
SEQUENCE: 46
gacacgcgag ctgagtcgga gacacgcagg gatgagatgg                              40

SEQ ID NO: 47              moltype = DNA  length = 40
FEATURE                    Location/Qualifiers
misc_feature               1..40
                           note = Description of Artificial Sequence: Syntheticprimer
source                     1..40
                           mol_type = other DNA
                           organism = synthetic construct
SEQUENCE: 47
gctgatacta ctgagtcgga gacacgcagg gatgagatgg                              40

SEQ ID NO: 48              moltype = DNA  length = 40
FEATURE                    Location/Qualifiers
misc_feature               1..40
                           note = Description of Artificial Sequence: Syntheticprimer
source                     1..40
                           mol_type = other DNA
                           organism = synthetic construct
SEQUENCE: 48
cgcatagaga ctgagtcgga gacacgcagg gatgagatgg                              40

SEQ ID NO: 49              moltype = DNA  length = 40
FEATURE                    Location/Qualifiers
misc_feature               1..40
                           note = Description of Artificial Sequence: Syntheticprimer
source                     1..40
```

-continued

```
                          mol_type = other DNA
                          organism = synthetic construct
SEQUENCE: 49
agacgtatca ctgagtcgga gacacgcagg gatgagatgg                          40

SEQ ID NO: 50            moltype = DNA  length = 40
FEATURE                  Location/Qualifiers
misc_feature             1..40
                         note = Description of Artificial Sequence: Syntheticprimer
source                   1..40
                         mol_type = other DNA
                         organism = synthetic construct
SEQUENCE: 50
tagctcagta ctgagtcgga gacacgcagg gatgagatgg                          40

SEQ ID NO: 51            moltype = DNA  length = 40
FEATURE                  Location/Qualifiers
misc_feature             1..40
                         note = Description of Artificial Sequence: Syntheticprimer
source                   1..40
                         mol_type = other DNA
                         organism = synthetic construct
SEQUENCE: 51
cactactatg ctgagtcgga gacacgcagg gatgagatgg                          40

SEQ ID NO: 52            moltype = DNA  length = 40
FEATURE                  Location/Qualifiers
misc_feature             1..40
                         note = Description of Artificial Sequence: Syntheticprimer
source                   1..40
                         mol_type = other DNA
                         organism = synthetic construct
SEQUENCE: 52
gtatctctcg ctgagtcgga gacacgcagg gatgagatgg                          40

SEQ ID NO: 53            moltype = DNA  length = 40
FEATURE                  Location/Qualifiers
misc_feature             1..40
                         note = Description of Artificial Sequence: Syntheticprimer
source                   1..40
                         mol_type = other DNA
                         organism = synthetic construct
SEQUENCE: 53
tacgtcgtat ctgagtcgga gacacgcagg gatgagatgg                          40

SEQ ID NO: 54            moltype = DNA  length = 40
FEATURE                  Location/Qualifiers
misc_feature             1..40
                         note = Description of Artificial Sequence: Syntheticprimer
source                   1..40
                         mol_type = other DNA
                         organism = synthetic construct
SEQUENCE: 54
tagtacgtga ctgagtcgga gacacgcagg gatgagatgg                          40

SEQ ID NO: 55            moltype = DNA  length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 55
ccatctcatc cctgcgtgtc tccgactcag acgagtgcgt acactgacga catggttcta   60
ca                                                                   62

SEQ ID NO: 56            moltype = DNA  length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 56
ccatctcatc cctgcgtgtc tccgactcag acgctcgaca acactgacga catggttcta   60
ca                                                                   62

SEQ ID NO: 57            moltype = DNA  length = 62
FEATURE                  Location/Qualifiers
```

-continued

```
misc_feature          1..62
                      note = Description of Artificial Sequence: Syntheticprimer
source                1..62
                      mol_type = other DNA
                      organism = synthetic construct
SEQUENCE: 57
ccatctcatc cctgcgtgtc tccgactcag agacgcactc acactgacga catggttcta  60
ca                                                                 62

SEQ ID NO: 58         moltype = DNA  length = 62
FEATURE               Location/Qualifiers
misc_feature          1..62
                      note = Description of Artificial Sequence: Syntheticprimer
source                1..62
                      mol_type = other DNA
                      organism = synthetic construct
SEQUENCE: 58
ccatctcatc cctgcgtgtc tccgactcag agcactgtag acactgacga catggttcta  60
ca                                                                 62

SEQ ID NO: 59         moltype = DNA  length = 62
FEATURE               Location/Qualifiers
misc_feature          1..62
                      note = Description of Artificial Sequence: Syntheticprimer
source                1..62
                      mol_type = other DNA
                      organism = synthetic construct
SEQUENCE: 59
ccatctcatc cctgcgtgtc tccgactcag atcagacacg acactgacga catggttcta  60
ca                                                                 62

SEQ ID NO: 60         moltype = DNA  length = 62
FEATURE               Location/Qualifiers
misc_feature          1..62
                      note = Description of Artificial Sequence: Syntheticprimer
source                1..62
                      mol_type = other DNA
                      organism = synthetic construct
SEQUENCE: 60
ccatctcatc cctgcgtgtc tccgactcag atatcgcgag acactgacga catggttcta  60
ca                                                                 62

SEQ ID NO: 61         moltype = DNA  length = 62
FEATURE               Location/Qualifiers
misc_feature          1..62
                      note = Description of Artificial Sequence: Syntheticprimer
source                1..62
                      mol_type = other DNA
                      organism = synthetic construct
SEQUENCE: 61
ccatctcatc cctgcgtgtc tccgactcag cgtgtctcta acactgacga catggttcta  60
ca                                                                 62

SEQ ID NO: 62         moltype = DNA  length = 62
FEATURE               Location/Qualifiers
misc_feature          1..62
                      note = Description of Artificial Sequence: Syntheticprimer
source                1..62
                      mol_type = other DNA
                      organism = synthetic construct
SEQUENCE: 62
ccatctcatc cctgcgtgtc tccgactcag ctcgcgtgtc acactgacga catggttcta  60
ca                                                                 62

SEQ ID NO: 63         moltype = DNA  length = 62
FEATURE               Location/Qualifiers
misc_feature          1..62
                      note = Description of Artificial Sequence: Syntheticprimer
source                1..62
                      mol_type = other DNA
                      organism = synthetic construct
SEQUENCE: 63
ccatctcatc cctgcgtgtc tccgactcag tagtatcagc acactgacga catggttcta  60
ca                                                                 62

SEQ ID NO: 64         moltype = DNA  length = 62
FEATURE               Location/Qualifiers
misc_feature          1..62
                      note = Description of Artificial Sequence: Syntheticprimer
```

```
source                    1..62
                          mol_type = other DNA
                          organism = synthetic construct
SEQUENCE: 64
ccatctcatc cctgcgtgtc tccgactcag tctctatgcg acactgacga catggttcta  60
ca                                                                  62

SEQ ID NO: 65             moltype = DNA   length = 62
FEATURE                   Location/Qualifiers
misc_feature              1..62
                          note = Description of Artificial Sequence: Syntheticprimer
source                    1..62
                          mol_type = other DNA
                          organism = synthetic construct
SEQUENCE: 65
ccatctcatc cctgcgtgtc tccgactcag tgatacgtct acactgacga catggttcta  60
ca                                                                  62

SEQ ID NO: 66             moltype = DNA   length = 62
FEATURE                   Location/Qualifiers
misc_feature              1..62
                          note = Description of Artificial Sequence: Syntheticprimer
source                    1..62
                          mol_type = other DNA
                          organism = synthetic construct
SEQUENCE: 66
ccatctcatc cctgcgtgtc tccgactcag tactgagcta acactgacga catggttcta  60
ca                                                                  62

SEQ ID NO: 67             moltype = DNA   length = 62
FEATURE                   Location/Qualifiers
misc_feature              1..62
                          note = Description of Artificial Sequence: Syntheticprimer
source                    1..62
                          mol_type = other DNA
                          organism = synthetic construct
SEQUENCE: 67
ccatctcatc cctgcgtgtc tccgactcag catagtagtg acactgacga catggttcta  60
ca                                                                  62

SEQ ID NO: 68             moltype = DNA   length = 62
FEATURE                   Location/Qualifiers
misc_feature              1..62
                          note = Description of Artificial Sequence: Syntheticprimer
source                    1..62
                          mol_type = other DNA
                          organism = synthetic construct
SEQUENCE: 68
ccatctcatc cctgcgtgtc tccgactcag cgagagatac acactgacga catggttcta  60
ca                                                                  62

SEQ ID NO: 69             moltype = DNA   length = 62
FEATURE                   Location/Qualifiers
misc_feature              1..62
                          note = Description of Artificial Sequence: Syntheticprimer
source                    1..62
                          mol_type = other DNA
                          organism = synthetic construct
SEQUENCE: 69
ccatctcatc cctgcgtgtc tccgactcag atacgacgta acactgacga catggttcta  60
ca                                                                  62

SEQ ID NO: 70             moltype = DNA   length = 62
FEATURE                   Location/Qualifiers
misc_feature              1..62
                          note = Description of Artificial Sequence: Syntheticprimer
source                    1..62
                          mol_type = other DNA
                          organism = synthetic construct
SEQUENCE: 70
ccatctcatc cctgcgtgtc tccgactcag tcacgtacta acactgacga catggttcta  60
ca                                                                  62

SEQ ID NO: 71             moltype = DNA   length = 45
FEATURE                   Location/Qualifiers
misc_feature              1..45
                          note = Description of Artificial Sequence: Syntheticprimer
source                    1..45
                          mol_type = other DNA
```

```
                          organism = synthetic construct
SEQUENCE: 71
cctctctatg ggcagtcggt gattacggta gcagagactt ggtct                            45

SEQ ID NO: 72            moltype = DNA   length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 72
ccatctcatc cctgcgtgtc tccgactcag acgagtgcgt tacggtagca gagacttggt   60
ct                                                                           62

SEQ ID NO: 73            moltype = DNA   length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 73
ccatctcatc cctgcgtgtc tccgactcag acgctcgaca tacggtagca gagacttggt   60
ct                                                                           62

SEQ ID NO: 74            moltype = DNA   length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 74
ccatctcatc cctgcgtgtc tccgactcag agacgcactc tacggtagca gagacttggt   60
ct                                                                           62

SEQ ID NO: 75            moltype = DNA   length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 75
ccatctcatc cctgcgtgtc tccgactcag agcactgtag tacggtagca gagacttggt   60
ct                                                                           62

SEQ ID NO: 76            moltype = DNA   length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 76
ccatctcatc cctgcgtgtc tccgactcag atcagacacg tacggtagca gagacttggt   60
ct                                                                           62

SEQ ID NO: 77            moltype = DNA   length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 77
ccatctcatc cctgcgtgtc tccgactcag atatcgcgag tacggtagca gagacttggt   60
ct                                                                           62

SEQ ID NO: 78            moltype = DNA   length = 62
FEATURE                  Location/Qualifiers
misc_feature             1..62
                         note = Description of Artificial Sequence: Syntheticprimer
source                   1..62
                         mol_type = other DNA
                         organism = synthetic construct
SEQUENCE: 78
ccatctcatc cctgcgtgtc tccgactcag cgtgtctcta tacggtagca gagacttggt   60
```

-continued

```
ct                                                                    62

SEQ ID NO: 79              moltype = DNA   length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 79
ccatctcatc cctgcgtgtc tccgactcag ctcgcgtgtc tacggtagca gagacttggt   60
ct                                                                    62

SEQ ID NO: 80              moltype = DNA   length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 80
ccatctcatc cctgcgtgtc tccgactcag tagtatcagc tacggtagca gagacttggt   60
ct                                                                    62

SEQ ID NO: 81              moltype = DNA   length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 81
ccatctcatc cctgcgtgtc tccgactcag tctctatgcg tacggtagca gagacttggt   60
ct                                                                    62

SEQ ID NO: 82              moltype = DNA   length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 82
ccatctcatc cctgcgtgtc tccgactcag tgatacgtct tacggtagca gagacttggt   60
ct                                                                    62

SEQ ID NO: 83              moltype = DNA   length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 83
ccatctcatc cctgcgtgtc tccgactcag tactgagcta tacggtagca gagacttggt   60
ct                                                                    62

SEQ ID NO: 84              moltype = DNA   length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 84
ccatctcatc cctgcgtgtc tccgactcag catagtagtg tacggtagca gagacttggt   60
ct                                                                    62

SEQ ID NO: 85              moltype = DNA   length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 85
ccatctcatc cctgcgtgtc tccgactcag cgagagatac tacggtagca gagacttggt   60
ct                                                                    62
```

```
SEQ ID NO: 86              moltype = DNA  length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 86
ccatctcatc cctgcgtgtc tccgactcag atacgacgta tacggtagca gagacttggt    60
ct                                                                    62

SEQ ID NO: 87              moltype = DNA  length = 62
FEATURE                    Location/Qualifiers
misc_feature               1..62
                           note = Description of Artificial Sequence: Syntheticprimer
source                     1..62
                           mol_type = other DNA
                           organism = synthetic construct
SEQUENCE: 87
ccatctcatc cctgcgtgtc tccgactcag tcacgtacta tacggtagca gagacttggt    60
ct                                                                    62

SEQ ID NO: 88              moltype = DNA  length = 45
FEATURE                    Location/Qualifiers
misc_feature               1..45
                           note = Description of Artificial Sequence: Syntheticprimer
source                     1..45
                           mol_type = other DNA
                           organism = synthetic construct
SEQUENCE: 88
cctctctatg ggcagtcggt gatacactga cgacatggtt ctaca                    45

SEQ ID NO: 89              moltype = DNA  length = 17
FEATURE                    Location/Qualifiers
misc_feature               1..17
                           note = Description of Artificial Sequence: Syntheticprimer
source                     1..17
                           mol_type = other DNA
                           organism = synthetic construct
SEQUENCE: 89
ggcggacggg tgagtaa                                                    17

SEQ ID NO: 90              moltype = DNA  length = 17
FEATURE                    Location/Qualifiers
misc_feature               1..17
                           note = Description of Artificial Sequence: Syntheticprimer
source                     1..17
                           mol_type = other DNA
                           organism = synthetic construct
SEQUENCE: 90
ggcgaacggg tgagtaa                                                    17

SEQ ID NO: 91              moltype = DNA  length = 17
FEATURE                    Location/Qualifiers
misc_feature               1..17
                           note = Description of Artificial Sequence: Syntheticprimer
source                     1..17
                           mol_type = other DNA
                           organism = synthetic construct
SEQUENCE: 91
ggcgcacggg tgagtaa                                                    17

SEQ ID NO: 92              moltype = DNA  length = 17
FEATURE                    Location/Qualifiers
misc_feature               1..17
                           note = Description of Artificial Sequence: Syntheticprimer
source                     1..17
                           mol_type = other DNA
                           organism = synthetic construct
SEQUENCE: 92
ggcggatggg tgagtaa                                                    17

SEQ ID NO: 93              moltype = DNA  length = 17
FEATURE                    Location/Qualifiers
misc_feature               1..17
                           note = Description of Artificial Sequence: Syntheticprimer
source                     1..17
                           mol_type = other DNA
                           organism = synthetic construct
```

```
SEQUENCE: 93
ggcaaacggg tgagtaa                                                17

SEQ ID NO: 94           moltype = DNA   length = 17
FEATURE                 Location/Qualifiers
misc_feature            1..17
                        note = Description of Artificial Sequence: Syntheticprimer
source                  1..17
                        mol_type = other DNA
                        organism = synthetic construct
SEQUENCE: 94
ggcgaacggg cgagtaa                                                17

SEQ ID NO: 95           moltype = DNA   length = 17
FEATURE                 Location/Qualifiers
misc_feature            1..17
                        note = Description of Artificial Sequence: Syntheticprimer
source                  1..17
                        mol_type = other DNA
                        organism = synthetic construct
SEQUENCE: 95
ggcgaacggc tgagtaa                                                17

SEQ ID NO: 96           moltype = DNA   length = 18
FEATURE                 Location/Qualifiers
misc_feature            1..18
                        note = Description of Artificial Sequence: Syntheticprimer
source                  1..18
                        mol_type = other DNA
                        organism = synthetic construct
SEQUENCE: 96
cactgctgcc tcccgtag                                               18

SEQ ID NO: 97           moltype = DNA   length = 18
FEATURE                 Location/Qualifiers
misc_feature            1..18
                        note = Description of Artificial Sequence: Syntheticprimer
source                  1..18
                        mol_type = other DNA
                        organism = synthetic construct
SEQUENCE: 97
tactgctgcc tcccgtag                                               18

SEQ ID NO: 98           moltype = DNA   length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 98
gacacggtcc agactcctac                                             20

SEQ ID NO: 99           moltype = DNA   length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 99
gacacggccc agactcctac                                             20

SEQ ID NO: 100          moltype = DNA   length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 100
gacacggtcc aaactcctac                                             20

SEQ ID NO: 101          moltype = DNA   length = 20
FEATURE                 Location/Qualifiers
misc_feature            1..20
                        note = Description of Artificial Sequence: Syntheticprimer
source                  1..20
                        mol_type = other DNA
```

-continued

```
                          organism = synthetic construct
SEQUENCE: 101
gacacggccc aaactcctac                                          20

SEQ ID NO: 102           moltype = DNA   length = 20
FEATURE                  Location/Qualifiers
misc_feature             1..20
                         note = Description of Artificial Sequence: Syntheticprimer
source                   1..20
                         mol_type = other DNA
                         organism = synthetic construct
SEQUENCE: 102
gatacggccc agactcctac                                          20

SEQ ID NO: 103           moltype = DNA   length = 16
FEATURE                  Location/Qualifiers
misc_feature             1..16
                         note = Description of Artificial Sequence: Syntheticprimer
source                   1..16
                         mol_type = other DNA
                         organism = synthetic construct
SEQUENCE: 103
attaccgcgg ctgctg                                              16

SEQ ID NO: 104           moltype = DNA   length = 39
FEATURE                  Location/Qualifiers
misc_feature             1..39
                         note = Description of Artificial Sequence: Syntheticprimer
source                   1..39
                         mol_type = other DNA
                         organism = synthetic construct
SEQUENCE: 104
acactgacga catggttcta caggcggacg ggtgagtaa                     39

SEQ ID NO: 105           moltype = DNA   length = 39
FEATURE                  Location/Qualifiers
misc_feature             1..39
                         note = Description of Artificial Sequence: Syntheticprimer
source                   1..39
                         mol_type = other DNA
                         organism = synthetic construct
SEQUENCE: 105
acactgacga catggttcta caggcgaacg ggtgagtaa                     39

SEQ ID NO: 106           moltype = DNA   length = 39
FEATURE                  Location/Qualifiers
misc_feature             1..39
                         note = Description of Artificial Sequence: Syntheticprimer
source                   1..39
                         mol_type = other DNA
                         organism = synthetic construct
SEQUENCE: 106
acactgacga catggttcta caggcgcacg ggtgagtaa                     39

SEQ ID NO: 107           moltype = DNA   length = 39
FEATURE                  Location/Qualifiers
misc_feature             1..39
                         note = Description of Artificial Sequence: Syntheticprimer
source                   1..39
                         mol_type = other DNA
                         organism = synthetic construct
SEQUENCE: 107
acactgacga catggttcta caggcggatg ggtgagtaa                     39

SEQ ID NO: 108           moltype = DNA   length = 39
FEATURE                  Location/Qualifiers
misc_feature             1..39
                         note = Description of Artificial Sequence: Syntheticprimer
source                   1..39
                         mol_type = other DNA
                         organism = synthetic construct
SEQUENCE: 108
acactgacga catggttcta caggcaaacg ggtgagtaa                     39

SEQ ID NO: 109           moltype = DNA   length = 39
FEATURE                  Location/Qualifiers
misc_feature             1..39
                         note = Description of Artificial Sequence: Syntheticprimer
source                   1..39
```

-continued

```
                              mol_type = other DNA
                              organism = synthetic construct
SEQUENCE: 109
acactgacga catggttcta caggcgaacg ggcgagtaa                        39

SEQ ID NO: 110         moltype = DNA   length = 39
FEATURE                Location/Qualifiers
misc_feature           1..39
                       note = Description of Artificial Sequence: Syntheticprimer
source                 1..39
                       mol_type = other DNA
                       organism = synthetic construct
SEQUENCE: 110
acactgacga catggttcta caggcgaacg gctgagtaa                        39

SEQ ID NO: 111         moltype = DNA   length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 111
tacggtagca gagacttggt ctcactgctg cctcccgtag                       40

SEQ ID NO: 112         moltype = DNA   length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 112
tacggtagca gagacttggt cttactgctg cctcccgtag                       40

SEQ ID NO: 113         moltype = DNA   length = 42
FEATURE                Location/Qualifiers
misc_feature           1..42
                       note = Description of Artificial Sequence: Syntheticprimer
source                 1..42
                       mol_type = other DNA
                       organism = synthetic construct
SEQUENCE: 113
acactgacga catggttcta cagacacggt ccagactcct ac                    42

SEQ ID NO: 114         moltype = DNA   length = 42
FEATURE                Location/Qualifiers
misc_feature           1..42
                       note = Description of Artificial Sequence: Syntheticprimer
source                 1..42
                       mol_type = other DNA
                       organism = synthetic construct
SEQUENCE: 114
acactgacga catggttcta cagacacggc ccagactcct ac                    42

SEQ ID NO: 115         moltype = DNA   length = 42
FEATURE                Location/Qualifiers
misc_feature           1..42
                       note = Description of Artificial Sequence: Syntheticprimer
source                 1..42
                       mol_type = other DNA
                       organism = synthetic construct
SEQUENCE: 115
acactgacga catggttcta cagacacggt ccaaactcct ac                    42

SEQ ID NO: 116         moltype = DNA   length = 42
FEATURE                Location/Qualifiers
misc_feature           1..42
                       note = Description of Artificial Sequence: Syntheticprimer
source                 1..42
                       mol_type = other DNA
                       organism = synthetic construct
SEQUENCE: 116
acactgacga catggttcta cagacacggc ccaaactcct ac                    42

SEQ ID NO: 117         moltype = DNA   length = 42
FEATURE                Location/Qualifiers
misc_feature           1..42
                       note = Description of Artificial Sequence: Syntheticprimer
```

```
source                  1..42
                        mol_type = other DNA
                        organism = synthetic construct
SEQUENCE: 117
acactgacga catggttcta cagatacggc ccagactcct ac                          42

SEQ ID NO: 118          moltype = DNA   length = 38
FEATURE                 Location/Qualifiers
misc_feature            1..38
                        note = Description of Artificial Sequence: Syntheticprimer
source                  1..38
                        mol_type = other DNA
                        organism = synthetic construct
SEQUENCE: 118
tacggtagca gagacttggt ctattaccgc ggctgctg                               38

SEQ ID NO: 119          moltype = DNA   length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 119
aaactcggtc atttagagga agtaa                                             25

SEQ ID NO: 120          moltype = DNA   length = 19
FEATURE                 Location/Qualifiers
misc_feature            1..19
                        note = Description of Artificial Sequence: Syntheticprimer
source                  1..19
                        mol_type = other DNA
                        organism = synthetic construct
SEQUENCE: 120
gatgccggaa ccaagagat                                                    19

SEQ ID NO: 121          moltype = DNA   length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 121
aacctcccac ccgtgtttat                                                   20

SEQ ID NO: 122          moltype = DNA   length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 122
atttcgctgc gttcttcatc                                                   20

SEQ ID NO: 123          moltype = DNA   length = 25
FEATURE                 Location/Qualifiers
misc_feature            1..25
                        note = Description of Artificial Sequence: Syntheticprimer
source                  1..25
                        mol_type = other DNA
                        organism = synthetic construct
SEQUENCE: 123
aaactcggtc atttagagga agtaa                                             25

SEQ ID NO: 124          moltype = DNA   length = 19
FEATURE                 Location/Qualifiers
misc_feature            1..19
                        note = Description of Artificial Sequence: Syntheticprimer
source                  1..19
                        mol_type = other DNA
                        organism = synthetic construct
SEQUENCE: 124
gctgcgttct tcatcgatg                                                    19

SEQ ID NO: 125          moltype = DNA   length = 20
FEATURE                 Location/Qualifiers
misc_feature            1..20
```

```
                        note = Description of Artificial Sequence: Syntheticprimer
source                  1..20
                        mol_type = other DNA
                        organism = synthetic construct
SEQUENCE: 125
atcgagtctt tgaacgcaca                                              20

SEQ ID NO: 126          moltype = DNA  length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 126
cctacctgat ccgaggtcaa                                              20

SEQ ID NO: 127          moltype = DNA  length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 127
tcgagtcttt gaacgcacat                                              20

SEQ ID NO: 128          moltype = DNA  length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 128
cgggtatccc tacctgatcc                                              20

SEQ ID NO: 129          moltype = DNA  length = 65
FEATURE                 Location/Qualifiers
misc_feature            1..65
                        note = Description of Artificial Sequence: Syntheticprimer
source                  1..65
                        mol_type = other DNA
                        organism = synthetic construct
SEQUENCE: 129
ccatctcatc cctgcgtgtc tccgactcag acgagtgcgt aaactcggtc atttagagga  60
agtaa                                                             65

SEQ ID NO: 130          moltype = DNA  length = 42
FEATURE                 Location/Qualifiers
misc_feature            1..42
                        note = Description of Artificial Sequence: Syntheticprimer
source                  1..42
                        mol_type = other DNA
                        organism = synthetic construct
SEQUENCE: 130
cctctctatg ggcagtcggt gatgatgccg gaaccaagag at                    42

SEQ ID NO: 131          moltype = DNA  length = 60
FEATURE                 Location/Qualifiers
misc_feature            1..60
                        note = Description of Artificial Sequence: Syntheticprimer
source                  1..60
                        mol_type = other DNA
                        organism = synthetic construct
SEQUENCE: 131
ccatctcatc cctgcgtgtc tccgactcag acgagtgcgt aacctcccac ccgtgtttat  60

SEQ ID NO: 132          moltype = DNA  length = 43
FEATURE                 Location/Qualifiers
misc_feature            1..43
                        note = Description of Artificial Sequence: Syntheticprimer
source                  1..43
                        mol_type = other DNA
                        organism = synthetic construct
SEQUENCE: 132
cctctctatg ggcagtcggt gatatttcgc tgcgttcttc atc                   43

SEQ ID NO: 133          moltype = DNA  length = 65
```

-continued

```
FEATURE                    Location/Qualifiers
misc_feature               1..65
                           note = Description of Artificial Sequence: Syntheticprimer
source                     1..65
                           mol_type = other DNA
                           organism = synthetic construct
SEQUENCE: 133
ccatctcatc cctgcgtgtc tccgactcag acgagtgcgt aaactcggtc atttagagga   60
agtaa                                                              65

SEQ ID NO: 134             moltype = DNA  length = 42
FEATURE                    Location/Qualifiers
misc_feature               1..42
                           note = Description of Artificial Sequence: Syntheticprimer
source                     1..42
                           mol_type = other DNA
                           organism = synthetic construct
SEQUENCE: 134
cctctctatg ggcagtcggt gatgctgcgt tcttcatcga tg                      42

SEQ ID NO: 135             moltype = DNA  length = 60
FEATURE                    Location/Qualifiers
misc_feature               1..60
                           note = Description of Artificial Sequence: Syntheticprimer
source                     1..60
                           mol_type = other DNA
                           organism = synthetic construct
SEQUENCE: 135
ccatctcatc cctgcgtgtc tccgactcag acgagtgcgt atcgagtctt tgaacgcaca   60

SEQ ID NO: 136             moltype = DNA  length = 43
FEATURE                    Location/Qualifiers
misc_feature               1..43
                           note = Description of Artificial Sequence: Syntheticprimer
source                     1..43
                           mol_type = other DNA
                           organism = synthetic construct
SEQUENCE: 136
cctctctatg ggcagtcggt gatcctacct gatccgaggt caa                     43

SEQ ID NO: 137             moltype = DNA  length = 60
FEATURE                    Location/Qualifiers
misc_feature               1..60
                           note = Description of Artificial Sequence: Syntheticprimer
source                     1..60
                           mol_type = other DNA
                           organism = synthetic construct
SEQUENCE: 137
ccatctcatc cctgcgtgtc tccgactcag acgagtgcgt tcgagtcttt gaacgcacat   60

SEQ ID NO: 138             moltype = DNA  length = 43
FEATURE                    Location/Qualifiers
misc_feature               1..43
                           note = Description of Artificial Sequence: Syntheticprimer
source                     1..43
                           mol_type = other DNA
                           organism = synthetic construct
SEQUENCE: 138
cctctctatg ggcagtcggt gatcgggtat ccctacctga tcc                     43

SEQ ID NO: 139             moltype = DNA  length = 17
FEATURE                    Location/Qualifiers
misc_feature               1..17
                           note = Description of Artificial Sequence: Syntheticprimer
source                     1..17
                           mol_type = other DNA
                           organism = synthetic construct
SEQUENCE: 139
gcaaggtcac cccgaag                                                  17

SEQ ID NO: 140             moltype = DNA  length = 17
FEATURE                    Location/Qualifiers
misc_feature               1..17
                           note = Description of Artificial Sequence: Syntheticprimer
source                     1..17
                           mol_type = other DNA
                           organism = synthetic construct
SEQUENCE: 140
cgatgacgcc cttgttg                                                  17
```

-continued

```
SEQ ID NO: 141          moltype = DNA   length = 19
FEATURE                 Location/Qualifiers
misc_feature            1..19
                        note = Description of Artificial Sequence: Syntheticprimer
source                  1..19
                        mol_type = other DNA
                        organism = synthetic construct
SEQUENCE: 141
ggcaaggtca ccccgaagg                                              19

SEQ ID NO: 142          moltype = DNA   length = 18
FEATURE                 Location/Qualifiers
misc_feature            1..18
                        note = Description of Artificial Sequence: Syntheticprimer
source                  1..18
                        mol_type = other DNA
                        organism = synthetic construct
SEQUENCE: 142
aggatcttgc cgatgacg                                               18

SEQ ID NO: 143          moltype = DNA   length = 17
FEATURE                 Location/Qualifiers
misc_feature            1..17
                        note = Description of Artificial Sequence: Syntheticprimer
source                  1..17
                        mol_type = other DNA
                        organism = synthetic construct
SEQUENCE: 143
gacgccacgg caacaag                                                17

SEQ ID NO: 144          moltype = DNA   length = 16
FEATURE                 Location/Qualifiers
misc_feature            1..16
                        note = Description of Artificial Sequence: Syntheticprimer
source                  1..16
                        mol_type = other DNA
                        organism = synthetic construct
SEQUENCE: 144
acgccacggc aacaag                                                 16

SEQ ID NO: 145          moltype = DNA   length = 22
FEATURE                 Location/Qualifiers
misc_feature            1..22
                        note = Description of Artificial Sequence: Syntheticprimer
source                  1..22
                        mol_type = other DNA
                        organism = synthetic construct
SEQUENCE: 145
caagtggtgc agcttcagga tg                                          22

SEQ ID NO: 146          moltype = DNA   length = 22
FEATURE                 Location/Qualifiers
misc_feature            1..22
                        note = Description of Artificial Sequence: Syntheticprimer
source                  1..22
                        mol_type = other DNA
                        organism = synthetic construct
SEQUENCE: 146
cargtggtgc agcttcakga tg                                          22

SEQ ID NO: 147          moltype = DNA   length = 15
FEATURE                 Location/Qualifiers
misc_feature            1..15
                        note = Description of Artificial Sequence: Syntheticprimer
source                  1..15
                        mol_type = other DNA
                        organism = synthetic construct
SEQUENCE: 147
ggcgccgtcg aacac                                                  15

SEQ ID NO: 148          moltype = DNA   length = 15
FEATURE                 Location/Qualifiers
misc_feature            1..15
                        note = Description of Artificial Sequence: Syntheticprimer
source                  1..15
                        mol_type = other DNA
                        organism = synthetic construct
SEQUENCE: 148
```

-continued

```
ggcrccgtcg aacac                                                      15

SEQ ID NO: 149         moltype = DNA  length = 15
FEATURE                Location/Qualifiers
misc_feature           1..15
                       note = Description of Artificial Sequence: Syntheticprimer
source                 1..15
                       mol_type = other DNA
                       organism = synthetic construct
SEQUENCE: 149
ggcaccgtcg aacac                                                      15

SEQ ID NO: 150         moltype = DNA  length = 15
FEATURE                Location/Qualifiers
misc_feature           1..15
                       note = Description of Artificial Sequence: Syntheticprimer
source                 1..15
                       mol_type = other DNA
                       organism = synthetic construct
SEQUENCE: 150
ggcgccgtcg aacac                                                      15

SEQ ID NO: 151         moltype = DNA  length = 16
FEATURE                Location/Qualifiers
misc_feature           1..16
                       note = Description of Artificial Sequence: Syntheticprimer
source                 1..16
                       mol_type = other DNA
                       organism = synthetic construct
SEQUENCE: 151
caccccggtg ttcgac                                                     16

SEQ ID NO: 152         moltype = DNA  length = 20
FEATURE                Location/Qualifiers
misc_feature           1..20
                       note = Description of Artificial Sequence: Syntheticprimer
source                 1..20
                       mol_type = other DNA
                       organism = synthetic construct
SEQUENCE: 152
ctgggtgatc atcgagtacg                                                 20

SEQ ID NO: 153         moltype = DNA  length = 47
FEATURE                Location/Qualifiers
misc_feature           1..47
                       note = Description of Artificial Sequence: Syntheticprimer
source                 1..47
                       mol_type = other DNA
                       organism = synthetic construct
SEQUENCE: 153
ccatctcatc cctgcgtgtc tccgactcag gcaaggtcac cccgaag                   47

SEQ ID NO: 154         moltype = DNA  length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 154
cctctctatg ggcagtcggt gatcgatgac gcccttgttg                           40

SEQ ID NO: 155         moltype = DNA  length = 49
FEATURE                Location/Qualifiers
misc_feature           1..49
                       note = Description of Artificial Sequence: Syntheticprimer
source                 1..49
                       mol_type = other DNA
                       organism = synthetic construct
SEQUENCE: 155
ccatctcatc cctgcgtgtc tccgactcag ggcaaggtca ccccgaagg                 49

SEQ ID NO: 156         moltype = DNA  length = 41
FEATURE                Location/Qualifiers
misc_feature           1..41
                       note = Description of Artificial Sequence: Syntheticprimer
source                 1..41
                       mol_type = other DNA
                       organism = synthetic construct
```

```
SEQUENCE: 156
cctctctatg ggcagtcggt gataggatct tgccgatgac g                        41

SEQ ID NO: 157          moltype = DNA   length = 57
FEATURE                 Location/Qualifiers
misc_feature            1..57
                        note = Description of Artificial Sequence: Syntheticprimer
source                  1..57
                        mol_type = other DNA
                        organism = synthetic construct
SEQUENCE: 157
ccatctcatc cctgcgtgtc tccgactcag acgagtgcgt gcaaggtcac cccgaag       57

SEQ ID NO: 158          moltype = DNA   length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 158
cctctctatg ggcagtcggt gatgcaaggt caccccgaag                          40

SEQ ID NO: 159          moltype = DNA   length = 47
FEATURE                 Location/Qualifiers
misc_feature            1..47
                        note = Description of Artificial Sequence: Syntheticprimer
source                  1..47
                        mol_type = other DNA
                        organism = synthetic construct
SEQUENCE: 159
ccatctcatc cctgcgtgtc tccgactcag cgatgacgcc cttgttg                  47

SEQ ID NO: 160          moltype = DNA   length = 42
FEATURE                 Location/Qualifiers
misc_feature            1..42
                        note = Description of Artificial Sequence: Syntheticprimer
source                  1..42
                        mol_type = other DNA
                        organism = synthetic construct
SEQUENCE: 160
cctctctatg ggcagtcggt gatggcaagg tcaccccgaa gg                       42

SEQ ID NO: 161          moltype = DNA   length = 48
FEATURE                 Location/Qualifiers
misc_feature            1..48
                        note = Description of Artificial Sequence: Syntheticprimer
source                  1..48
                        mol_type = other DNA
                        organism = synthetic construct
SEQUENCE: 161
ccatctcatc cctgcgtgtc tccgactcag aggatcttgc cgatgacg                 48

SEQ ID NO: 162          moltype = DNA   length = 47
FEATURE                 Location/Qualifiers
misc_feature            1..47
                        note = Description of Artificial Sequence: Syntheticprimer
source                  1..47
                        mol_type = other DNA
                        organism = synthetic construct
SEQUENCE: 162
ccatctcatc cctgcgtgtc tccgactcag gacgccacgg caacaag                  47

SEQ ID NO: 163          moltype = DNA   length = 46
FEATURE                 Location/Qualifiers
misc_feature            1..46
                        note = Description of Artificial Sequence: Syntheticprimer
source                  1..46
                        mol_type = other DNA
                        organism = synthetic construct
SEQUENCE: 163
ccatctcatc cctgcgtgtc tccgactcag acgccacggc aacaag                   46

SEQ ID NO: 164          moltype = DNA   length = 45
FEATURE                 Location/Qualifiers
misc_feature            1..45
                        note = Description of Artificial Sequence: Syntheticprimer
source                  1..45
                        mol_type = other DNA
```

```
                        organism = synthetic construct
SEQUENCE: 164
cctctctatg ggcagtcggt gatcaagtgg tgcagcttca ggatg                        45

SEQ ID NO: 165        moltype = DNA  length = 45
FEATURE               Location/Qualifiers
misc_feature          1..45
                      note = Description of Artificial Sequence: Syntheticprimer
source                1..45
                      mol_type = other DNA
                      organism = synthetic construct
SEQUENCE: 165
cctctctatg ggcagtcggt gatcargtgg tgcagcttca kgatg                        45

SEQ ID NO: 166        moltype = DNA  length = 38
FEATURE               Location/Qualifiers
misc_feature          1..38
                      note = Description of Artificial Sequence: Syntheticprimer
source                1..38
                      mol_type = other DNA
                      organism = synthetic construct
SEQUENCE: 166
cctctctatg ggcagtcggt gatggcgccg tcgaacac                                38

SEQ ID NO: 167        moltype = DNA  length = 38
FEATURE               Location/Qualifiers
misc_feature          1..38
                      note = Description of Artificial Sequence: Syntheticprimer
source                1..38
                      mol_type = other DNA
                      organism = synthetic construct
SEQUENCE: 167
cctctctatg ggcagtcggt gatggcrccg tcgaacac                                38

SEQ ID NO: 168        moltype = DNA  length = 57
FEATURE               Location/Qualifiers
misc_feature          1..57
                      note = Description of Artificial Sequence: Syntheticprimer
source                1..57
                      mol_type = other DNA
                      organism = synthetic construct
SEQUENCE: 168
ccatctcatc cctgcgtgtc tccgactcag acgagtgcgt gacgccacgg caacaag         57

SEQ ID NO: 169        moltype = DNA  length = 56
FEATURE               Location/Qualifiers
misc_feature          1..56
                      note = Description of Artificial Sequence: Syntheticprimer
source                1..56
                      mol_type = other DNA
                      organism = synthetic construct
SEQUENCE: 169
ccatctcatc cctgcgtgtc tccgactcag acgagtgcgt acgccacggc aacaag          56

SEQ ID NO: 170        moltype = DNA  length = 40
FEATURE               Location/Qualifiers
misc_feature          1..40
                      note = Description of Artificial Sequence: Syntheticprimer
source                1..40
                      mol_type = other DNA
                      organism = synthetic construct
SEQUENCE: 170
cctctctatg ggcagtcggt gatgacgcca cggcaacaag                              40

SEQ ID NO: 171        moltype = DNA  length = 39
FEATURE               Location/Qualifiers
misc_feature          1..39
                      note = Description of Artificial Sequence: Syntheticprimer
source                1..39
                      mol_type = other DNA
                      organism = synthetic construct
SEQUENCE: 171
cctctctatg ggcagtcggt gatacgccac ggcaacaag                               39

SEQ ID NO: 172        moltype = DNA  length = 52
FEATURE               Location/Qualifiers
misc_feature          1..52
                      note = Description of Artificial Sequence: Syntheticprimer
source                1..52
```

-continued

```
                            mol_type = other DNA
                            organism = synthetic construct
SEQUENCE: 172
ccatctcatc cctgcgtgtc tccgactcag caagtggtgc agcttcagga tg            52

SEQ ID NO: 173          moltype = DNA   length = 52
FEATURE                 Location/Qualifiers
misc_feature            1..52
                        note = Description of Artificial Sequence: Syntheticprimer
source                  1..52
                        mol_type = other DNA
                        organism = synthetic construct
SEQUENCE: 173
ccatctcatc cctgcgtgtc tccgactcag cargtggtgc agcttcakga tg            52

SEQ ID NO: 174          moltype = DNA   length = 45
FEATURE                 Location/Qualifiers
misc_feature            1..45
                        note = Description of Artificial Sequence: Syntheticprimer
source                  1..45
                        mol_type = other DNA
                        organism = synthetic construct
SEQUENCE: 174
ccatctcatc cctgcgtgtc tccgactcag ggcgccgtcg aacac                    45

SEQ ID NO: 175          moltype = DNA   length = 45
FEATURE                 Location/Qualifiers
misc_feature            1..45
                        note = Description of Artificial Sequence: Syntheticprimer
source                  1..45
                        mol_type = other DNA
                        organism = synthetic construct
SEQUENCE: 175
ccatctcatc cctgcgtgtc tccgactcag ggcrccgtcg aacac                    45

SEQ ID NO: 176          moltype = DNA   length = 46
FEATURE                 Location/Qualifiers
misc_feature            1..46
                        note = Description of Artificial Sequence: Syntheticprimer
source                  1..46
                        mol_type = other DNA
                        organism = synthetic construct
SEQUENCE: 176
ccatctcatc cctgcgtgtc tccgactcag caccccggtg ttcgac                   46

SEQ ID NO: 177          moltype = DNA   length = 43
FEATURE                 Location/Qualifiers
misc_feature            1..43
                        note = Description of Artificial Sequence: Syntheticprimer
source                  1..43
                        mol_type = other DNA
                        organism = synthetic construct
SEQUENCE: 177
cctctctatg ggcagtcggt gatctgggtg atcatcgagt acg                      43

SEQ ID NO: 178          moltype = DNA   length = 56
FEATURE                 Location/Qualifiers
misc_feature            1..56
                        note = Description of Artificial Sequence: Syntheticprimer
source                  1..56
                        mol_type = other DNA
                        organism = synthetic construct
SEQUENCE: 178
ccatctcatc cctgcgtgtc tccgactcag acgagtgcgt caccccggtg ttcgac        56

SEQ ID NO: 179          moltype = DNA   length = 39
FEATURE                 Location/Qualifiers
misc_feature            1..39
                        note = Description of Artificial Sequence: Syntheticprimer
source                  1..39
                        mol_type = other DNA
                        organism = synthetic construct
SEQUENCE: 179
cctctctatg ggcagtcggt gatcaccccg gtgttcgac                           39

SEQ ID NO: 180          moltype = DNA   length = 50
FEATURE                 Location/Qualifiers
misc_feature            1..50
                        note = Description of Artificial Sequence: Syntheticprimer
```

-continued

```
source                   1..50
                         mol_type = other DNA
                         organism = synthetic construct
SEQUENCE: 180
ccatctcatc cctgcgtgtc tccgactcag ctgggtgatc atcgagtacg           50

SEQ ID NO: 181           moltype = DNA   length = 18
FEATURE                  Location/Qualifiers
misc_feature             1..18
                         note = Description of Artificial Sequence: Syntheticprimer
source                   1..18
                         mol_type = other DNA
                         organism = synthetic construct
SEQUENCE: 181
ccttgggacc tggtggtt                                              18

SEQ ID NO: 182           moltype = DNA   length = 18
FEATURE                  Location/Qualifiers
misc_feature             1..18
                         note = Description of Artificial Sequence: Syntheticprimer
source                   1..18
                         mol_type = other DNA
                         organism = synthetic construct
SEQUENCE: 182
ccttaggacc tggtggtt                                              18

SEQ ID NO: 183           moltype = DNA   length = 19
FEATURE                  Location/Qualifiers
misc_feature             1..19
                         note = Description of Artificial Sequence: Syntheticprimer
source                   1..19
                         mol_type = other DNA
                         organism = synthetic construct
SEQUENCE: 183
gctttaggtc ctggtggtt                                             19

SEQ ID NO: 184           moltype = DNA   length = 18
FEATURE                  Location/Qualifiers
misc_feature             1..18
                         note = Description of Artificial Sequence: Syntheticprimer
source                   1..18
                         mol_type = other DNA
                         organism = synthetic construct
SEQUENCE: 184
ccttggggcc tggtggtt                                              18

SEQ ID NO: 185           moltype = DNA   length = 18
FEATURE                  Location/Qualifiers
misc_feature             1..18
                         note = Description of Artificial Sequence: Syntheticprimer
source                   1..18
                         mol_type = other DNA
                         organism = synthetic construct
SEQUENCE: 185
ccttagggcc tggtggtt                                              18

SEQ ID NO: 186           moltype = DNA   length = 20
FEATURE                  Location/Qualifiers
misc_feature             1..20
                         note = Description of Artificial Sequence: Syntheticprimer
source                   1..20
                         mol_type = other DNA
                         organism = synthetic construct
SEQUENCE: 186
cttcttcgtc ggcagtcaac                                            20

SEQ ID NO: 187           moltype = DNA   length = 21
FEATURE                  Location/Qualifiers
misc_feature             1..21
                         note = Description of Artificial Sequence: Syntheticprimer
source                   1..21
                         mol_type = other DNA
                         organism = synthetic construct
SEQUENCE: 187
cttcttcatc agcagtcaac c                                          21

SEQ ID NO: 188           moltype = DNA   length = 20
FEATURE                  Location/Qualifiers
misc_feature             1..20
```

```
                              note = Description of Artificial Sequence: Syntheticprimer
source                        1..20
                              mol_type = other DNA
                              organism = synthetic construct
SEQUENCE: 188
cttcttcatc agcagttagc                                             20

SEQ ID NO: 189                moltype = DNA   length = 20
FEATURE                       Location/Qualifiers
misc_feature                  1..20
                              note = Description of Artificial Sequence: Syntheticprimer
source                        1..20
                              mol_type = other DNA
                              organism = synthetic construct
SEQUENCE: 189
cttcttcatc agcagtaagc                                             20

SEQ ID NO: 190                moltype = DNA   length = 20
FEATURE                       Location/Qualifiers
misc_feature                  1..20
                              note = Description of Artificial Sequence: Syntheticprimer
source                        1..20
                              mol_type = other DNA
                              organism = synthetic construct
SEQUENCE: 190
cttcttcatc agctgtcaac                                             20

SEQ ID NO: 191                moltype = DNA   length = 20
FEATURE                       Location/Qualifiers
misc_feature                  1..20
                              note = Description of Artificial Sequence: Syntheticprimer
source                        1..20
                              mol_type = other DNA
                              organism = synthetic construct
SEQUENCE: 191
cttcttcatc ggctgtcaac                                             20

SEQ ID NO: 192                moltype = DNA   length = 20
FEATURE                       Location/Qualifiers
misc_feature                  1..20
                              note = Description of Artificial Sequence: Syntheticprimer
source                        1..20
                              mol_type = other DNA
                              organism = synthetic construct
SEQUENCE: 192
cttcctcgtc agcggtcaac                                             20

SEQ ID NO: 193                moltype = DNA   length = 20
FEATURE                       Location/Qualifiers
misc_feature                  1..20
                              note = Description of Artificial Sequence: Syntheticprimer
source                        1..20
                              mol_type = other DNA
                              organism = synthetic construct
SEQUENCE: 193
cttcttcgtc cgctgtcagc                                             20

SEQ ID NO: 194                moltype = DNA   length = 20
FEATURE                       Location/Qualifiers
misc_feature                  1..20
                              note = Description of Artificial Sequence: Syntheticprimer
source                        1..20
                              mol_type = other DNA
                              organism = synthetic construct
SEQUENCE: 194
cttcttcatc cgctgttagc                                             20

SEQ ID NO: 195                moltype = DNA   length = 20
FEATURE                       Location/Qualifiers
misc_feature                  1..20
                              note = Description of Artificial Sequence: Syntheticprimer
source                        1..20
                              mol_type = other DNA
                              organism = synthetic construct
SEQUENCE: 195
tgcgacagca tgtattcctt                                             20

SEQ ID NO: 196                moltype = DNA   length = 20
FEATURE                       Location/Qualifiers
```

```
misc_feature            1..20
                        note = Description of Artificial Sequence: Syntheticprimer
source                  1..20
                        mol_type = other DNA
                        organism = synthetic construct
SEQUENCE: 196
cgcaacagca tgtattcctt                                                  20

SEQ ID NO: 197          moltype = DNA  length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 197
tgcaacggca tgtattcctt                                                  20

SEQ ID NO: 198          moltype = DNA  length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 198
ggcaacggca tgtattcctt                                                  20

SEQ ID NO: 199          moltype = DNA  length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 199
tgagtttgaa cgacggaatt t                                                21

SEQ ID NO: 200          moltype = DNA  length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 200
tgagttggag cgacggaatt t                                                21

SEQ ID NO: 201          moltype = DNA  length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 201
agagtttgaa cggcggaatt t                                                21

SEQ ID NO: 202          moltype = DNA  length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 202
agagttagaa cgacggaatt t                                                21

SEQ ID NO: 203          moltype = DNA  length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 203
tgagtttgaa cggcggaatt t                                                21

SEQ ID NO: 204          moltype = DNA  length = 21
```

-continued

```
FEATURE              Location/Qualifiers
misc_feature         1..21
                     note = Description of Artificial Sequence: Syntheticprimer
source               1..21
                     mol_type = other DNA
                     organism = synthetic construct
SEQUENCE: 204
tgagttagaa cgacggaatt t                                            21

SEQ ID NO: 205       moltype = DNA   length = 21
FEATURE              Location/Qualifiers
misc_feature         1..21
                     note = Description of Artificial Sequence: Syntheticprimer
source               1..21
                     mol_type = other DNA
                     organism = synthetic construct
SEQUENCE: 205
tgagttagaa cggcggaatt t                                            21

SEQ ID NO: 206       moltype = DNA   length = 21
FEATURE              Location/Qualifiers
misc_feature         1..21
                     note = Description of Artificial Sequence: Syntheticprimer
source               1..21
                     mol_type = other DNA
                     organism = synthetic construct
SEQUENCE: 206
tgaacatcgg tcaggttatg g                                            21

SEQ ID NO: 207       moltype = DNA   length = 21
FEATURE              Location/Qualifiers
misc_feature         1..21
                     note = Description of Artificial Sequence: Syntheticprimer
source               1..21
                     mol_type = other DNA
                     organism = synthetic construct
SEQUENCE: 207
tgaacattgg tcaggttatg g                                            21

SEQ ID NO: 208       moltype = DNA   length = 21
FEATURE              Location/Qualifiers
misc_feature         1..21
                     note = Description of Artificial Sequence: Syntheticprimer
source               1..21
                     mol_type = other DNA
                     organism = synthetic construct
SEQUENCE: 208
tgaatattgg tcaggttatg g                                            21

SEQ ID NO: 209       moltype = DNA   length = 21
FEATURE              Location/Qualifiers
misc_feature         1..21
                     note = Description of Artificial Sequence: Syntheticprimer
source               1..21
                     mol_type = other DNA
                     organism = synthetic construct
SEQUENCE: 209
tgaatatcgg tcaggttatg g                                            21

SEQ ID NO: 210       moltype = DNA   length = 21
FEATURE              Location/Qualifiers
misc_feature         1..21
                     note = Description of Artificial Sequence: Syntheticprimer
source               1..21
                     mol_type = other DNA
                     organism = synthetic construct
SEQUENCE: 210
tgaacatcgg acaagttatg g                                            21

SEQ ID NO: 211       moltype = DNA   length = 21
FEATURE              Location/Qualifiers
misc_feature         1..21
                     note = Description of Artificial Sequence: Syntheticprimer
source               1..21
                     mol_type = other DNA
                     organism = synthetic construct
SEQUENCE: 211
tgaacattgg acaggttatg g                                            21
```

-continued

```
SEQ ID NO: 212          moltype = DNA  length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 212
tgaacattgg gcaagttatg g                                           21

SEQ ID NO: 213          moltype = DNA  length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 213
tgaatatcgg acaagttatg g                                           21

SEQ ID NO: 214          moltype = DNA  length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 214
tgaatattgg tcaagttatg g                                           21

SEQ ID NO: 215          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 215
tgaagtttat catcaaccat gtg                                         23

SEQ ID NO: 216          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 216
tgcaatttat catcaaccat gtg                                         23

SEQ ID NO: 217          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 217
tgcaacttat catcaaccat gtg                                         23

SEQ ID NO: 218          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 218
tgaagcttat catctaccat gtg                                         23

SEQ ID NO: 219          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 219
tggagtttat catctaccat gtg                                         23
```

```
SEQ ID NO: 220          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 220
tgaagcttat catcaaccat gtg                                              23

SEQ ID NO: 221          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 221
tgcaatttat cgtcaaccat gtg                                              23

SEQ ID NO: 222          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 222
tggagcttat catcaaccat gtg                                              23

SEQ ID NO: 223          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 223
cttcaccaca tggttgatga taa                                              23

SEQ ID NO: 224          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 224
ctccaccaca tggttgatga taa                                              23

SEQ ID NO: 225          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 225
ctccaccaca tggttgacga taa                                              23

SEQ ID NO: 226          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 226
ctccaccaca tggtagatga taa                                              23

SEQ ID NO: 227          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 227
```

```
cttcaccaca tggtagatga taa                                          23

SEQ ID NO: 228          moltype = DNA   length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 228
ttctggtaca cctggttttg g                                            21

SEQ ID NO: 229          moltype = DNA   length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 229
ttctggcaca cctggttttg g                                            21

SEQ ID NO: 230          moltype = DNA   length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 230
ttctggaaca cctggttttg g                                            21

SEQ ID NO: 231          moltype = DNA   length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 231
ttctgggaca cctggttttg g                                            21

SEQ ID NO: 232          moltype = DNA   length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 232
ttctggtaca ccaggctttg g                                            21

SEQ ID NO: 233          moltype = DNA   length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 233
ttctggtacc cctggttttg g                                            21

SEQ ID NO: 234          moltype = DNA   length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 234
ccatctcatc cctgcgtgtc tccgactcag acgagtgcgt                        40

SEQ ID NO: 235          moltype = DNA   length = 40
FEATURE                 Location/Qualifiers
misc_feature            1..40
                        note = Description of Artificial Sequence: Syntheticprimer
source                  1..40
                        mol_type = other DNA
                        organism = synthetic construct
```

```
SEQUENCE: 235
ccatctcatc cctgcgtgtc tccgactcag acgagtgcgt                          40

SEQ ID NO: 236          moltype = DNA   length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 236
ccatctcatc cctgcgtgtc tccgactcag acgagtgcgt                          40

SEQ ID NO: 237          moltype = DNA   length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 237
ccatctcatc cctgcgtgtc tccgactcag acgagtgcgt                          40

SEQ ID NO: 238          moltype = DNA   length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 238
cctctctatg ggcagtcggt gat                                            23

SEQ ID NO: 239          moltype = DNA   length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 239
cctctctatg ggcagtcggt gat                                            23

SEQ ID NO: 240          moltype = DNA   length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 240
cctctctatg ggcagtcggt gat                                            23

SEQ ID NO: 241          moltype = DNA   length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 241
cctctctatg ggcagtcggt gat                                            23

SEQ ID NO: 242          moltype = DNA   length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 242
cctctctatg ggcagtcggt gat                                            23

SEQ ID NO: 243          moltype = DNA   length = 23
FEATURE                 Location/Qualifiers
misc_feature            1..23
                        note = Description of Artificial Sequence: Syntheticprimer
source                  1..23
                        mol_type = other DNA
```

```
                             organism = synthetic construct
SEQUENCE: 243
cctctctatg ggcagtcggt gat                                      23

SEQ ID NO: 244          moltype = DNA  length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 244
cctctctatg ggcagtcggt gat                                      23

SEQ ID NO: 245          moltype = DNA  length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 245
ccatctcatc cctgcgtgtc tccgactcag acgagtgcgt                    40

SEQ ID NO: 246          moltype = DNA  length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 246
ccatctcatc cctgcgtgtc tccgactcag acgagtgcgt                    40

SEQ ID NO: 247          moltype = DNA  length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 247
ccatctcatc cctgcgtgtc tccgactcag acgagtgcgt                    40

SEQ ID NO: 248          moltype = DNA  length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 248
ccatctcatc cctgcgtgtc tccgactcag acgagtgcgt                    40

SEQ ID NO: 249          moltype = DNA  length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 249
ccatctcatc cctgcgtgtc tccgactcag acgagtgcgt                    40

SEQ ID NO: 250          moltype = DNA  length = 40
FEATURE                 Location/Qualifiers
misc_feature            1..40
                        note = Description of Artificial Sequence: Syntheticprimer
source                  1..40
                        mol_type = other DNA
                        organism = synthetic construct
SEQUENCE: 250
ccatctcatc cctgcgtgtc tccgactcag acgagtgcgt                    40

SEQ ID NO: 251          moltype = DNA  length = 40
FEATURE                 Location/Qualifiers
misc_feature            1..40
                        note = Description of Artificial Sequence: Syntheticprimer
source                  1..40
```

-continued

```
                            mol_type = other DNA
                            organism = synthetic construct
SEQUENCE: 251
ccatctcatc cctgcgtgtc tccgactcag acgagtgcgt                      40

SEQ ID NO: 252         moltype = DNA   length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 252
ccatctcatc cctgcgtgtc tccgactcag acgagtgcgt                      40

SEQ ID NO: 253         moltype = DNA   length = 40
FEATURE                Location/Qualifiers
misc_feature           1..40
                       note = Description of Artificial Sequence: Syntheticprimer
source                 1..40
                       mol_type = other DNA
                       organism = synthetic construct
SEQUENCE: 253
ccatctcatc cctgcgtgtc tccgactcag acgagtgcgt                      40

SEQ ID NO: 254         moltype = DNA   length = 23
FEATURE                Location/Qualifiers
misc_feature           1..23
                       note = Description of Artificial Sequence: Syntheticprimer
source                 1..23
                       mol_type = other DNA
                       organism = synthetic construct
SEQUENCE: 254
cctctctatg ggcagtcggt gat                                        23

SEQ ID NO: 255         moltype = DNA   length = 23
FEATURE                Location/Qualifiers
misc_feature           1..23
                       note = Description of Artificial Sequence: Syntheticprimer
source                 1..23
                       mol_type = other DNA
                       organism = synthetic construct
SEQUENCE: 255
cctctctatg ggcagtcggt gat                                        23

SEQ ID NO: 256         moltype = DNA   length = 23
FEATURE                Location/Qualifiers
misc_feature           1..23
                       note = Description of Artificial Sequence: Syntheticprimer
source                 1..23
                       mol_type = other DNA
                       organism = synthetic construct
SEQUENCE: 256
cctctctatg ggcagtcggt gat                                        23

SEQ ID NO: 257         moltype = DNA   length = 23
FEATURE                Location/Qualifiers
misc_feature           1..23
                       note = Description of Artificial Sequence: Syntheticprimer
source                 1..23
                       mol_type = other DNA
                       organism = synthetic construct
SEQUENCE: 257
cctctctatg ggcagtcggt gat                                        23

SEQ ID NO: 258         moltype = DNA   length = 23
FEATURE                Location/Qualifiers
misc_feature           1..23
                       note = Description of Artificial Sequence: Syntheticprimer
source                 1..23
                       mol_type = other DNA
                       organism = synthetic construct
SEQUENCE: 258
cctctctatg ggcagtcggt gat                                        23

SEQ ID NO: 259         moltype = DNA   length = 23
FEATURE                Location/Qualifiers
misc_feature           1..23
                       note = Description of Artificial Sequence: Syntheticprimer
```

```
source                    1..23
                          mol_type = other DNA
                          organism = synthetic construct
SEQUENCE: 259
cctctctatg ggcagtcggt gat                                              23

SEQ ID NO: 260            moltype = DNA  length = 23
FEATURE                   Location/Qualifiers
misc_feature              1..23
                          note = Description of Artificial Sequence: Syntheticprimer
source                    1..23
                          mol_type = other DNA
                          organism = synthetic construct
SEQUENCE: 260
cctctctatg ggcagtcggt gat                                              23

SEQ ID NO: 261            moltype = DNA  length = 23
FEATURE                   Location/Qualifiers
misc_feature              1..23
                          note = Description of Artificial Sequence: Syntheticprimer
source                    1..23
                          mol_type = other DNA
                          organism = synthetic construct
SEQUENCE: 261
cctctctatg ggcagtcggt gat                                              23

SEQ ID NO: 262            moltype = DNA  length = 40
FEATURE                   Location/Qualifiers
misc_feature              1..40
                          note = Description of Artificial Sequence: Syntheticprimer
source                    1..40
                          mol_type = other DNA
                          organism = synthetic construct
SEQUENCE: 262
ccatctcatc cctgcgtgtc tccgactcag acgagtgcgt                            40

SEQ ID NO: 263            moltype = DNA  length = 40
FEATURE                   Location/Qualifiers
misc_feature              1..40
                          note = Description of Artificial Sequence: Syntheticprimer
source                    1..40
                          mol_type = other DNA
                          organism = synthetic construct
SEQUENCE: 263
ccatctcatc cctgcgtgtc tccgactcag acgagtgcgt                            40

SEQ ID NO: 264            moltype = DNA  length = 40
FEATURE                   Location/Qualifiers
misc_feature              1..40
                          note = Description of Artificial Sequence: Syntheticprimer
source                    1..40
                          mol_type = other DNA
                          organism = synthetic construct
SEQUENCE: 264
ccatctcatc cctgcgtgtc tccgactcag acgagtgcgt                            40

SEQ ID NO: 265            moltype = DNA  length = 40
FEATURE                   Location/Qualifiers
misc_feature              1..40
                          note = Description of Artificial Sequence: Syntheticprimer
source                    1..40
                          mol_type = other DNA
                          organism = synthetic construct
SEQUENCE: 265
ccatctcatc cctgcgtgtc tccgactcag acgagtgcgt                            40

SEQ ID NO: 266            moltype = DNA  length = 40
FEATURE                   Location/Qualifiers
misc_feature              1..40
                          note = Description of Artificial Sequence: Syntheticprimer
source                    1..40
                          mol_type = other DNA
                          organism = synthetic construct
SEQUENCE: 266
ccatctcatc cctgcgtgtc tccgactcag acgagtgcgt                            40

SEQ ID NO: 267            moltype = DNA  length = 23
FEATURE                   Location/Qualifiers
misc_feature              1..23
```

```
                              note = Description of Artificial Sequence: Syntheticprimer
source                        1..23
                              mol_type = other DNA
                              organism = synthetic construct
SEQUENCE: 267
cctctctatg ggcagtcggt gat                                                    23

SEQ ID NO: 268        moltype = DNA   length = 23
FEATURE               Location/Qualifiers
misc_feature          1..23
                      note = Description of Artificial Sequence: Syntheticprimer
source                1..23
                      mol_type = other DNA
                      organism = synthetic construct
SEQUENCE: 268
cctctctatg ggcagtcggt gat                                                    23

SEQ ID NO: 269        moltype = DNA   length = 23
FEATURE               Location/Qualifiers
misc_feature          1..23
                      note = Description of Artificial Sequence: Syntheticprimer
source                1..23
                      mol_type = other DNA
                      organism = synthetic construct
SEQUENCE: 269
cctctctatg ggcagtcggt gat                                                    23

SEQ ID NO: 270        moltype = DNA   length = 23
FEATURE               Location/Qualifiers
misc_feature          1..23
                      note = Description of Artificial Sequence: Syntheticprimer
source                1..23
                      mol_type = other DNA
                      organism = synthetic construct
SEQUENCE: 270
cctctctatg ggcagtcggt gat                                                    23

SEQ ID NO: 271        moltype = DNA   length = 23
FEATURE               Location/Qualifiers
misc_feature          1..23
                      note = Description of Artificial Sequence: Syntheticprimer
source                1..23
                      mol_type = other DNA
                      organism = synthetic construct
SEQUENCE: 271
cctctctatg ggcagtcggt gat                                                    23

SEQ ID NO: 272        moltype = DNA   length = 23
FEATURE               Location/Qualifiers
misc_feature          1..23
                      note = Description of Artificial Sequence: Syntheticprimer
source                1..23
                      mol_type = other DNA
                      organism = synthetic construct
SEQUENCE: 272
cctctctatg ggcagtcggt gat                                                    23

SEQ ID NO: 273        moltype = DNA   length = 24
FEATURE               Location/Qualifiers
misc_feature          1..24
                      note = Description of Artificial Sequence: Syntheticprimer
source                1..24
                      mol_type = other DNA
                      organism = synthetic construct
SEQUENCE: 273
gaaactacgc gagaatttca gaag                                                   24

SEQ ID NO: 274        moltype = DNA   length = 24
FEATURE               Location/Qualifiers
misc_feature          1..24
                      note = Description of Artificial Sequence: Syntheticprimer
source                1..24
                      mol_type = other DNA
                      organism = synthetic construct
SEQUENCE: 274
gaaattacgc gagaatttca gaag                                                   24

SEQ ID NO: 275        moltype = DNA   length = 24
FEATURE               Location/Qualifiers
```

-continued

```
misc_feature           1..24
                       note = Description of Artificial Sequence: Syntheticprimer
source                 1..24
                       mol_type = other DNA
                       organism = synthetic construct
SEQUENCE: 275
gaaattatgc gagaatttca gaag                                      24

SEQ ID NO: 276         moltype = DNA  length = 24
FEATURE                Location/Qualifiers
misc_feature           1..24
                       note = Description of Artificial Sequence: Syntheticprimer
source                 1..24
                       mol_type = other DNA
                       organism = synthetic construct
SEQUENCE: 276
gaaactatgc gagaatttca gagg                                      24

SEQ ID NO: 277         moltype = DNA  length = 22
FEATURE                Location/Qualifiers
misc_feature           1..22
                       note = Description of Artificial Sequence: Syntheticprimer
source                 1..22
                       mol_type = other DNA
                       organism = synthetic construct
SEQUENCE: 277
cgaagaggtg cagcataagt ag                                        22

SEQ ID NO: 278         moltype = DNA  length = 22
FEATURE                Location/Qualifiers
misc_feature           1..22
                       note = Description of Artificial Sequence: Syntheticprimer
source                 1..22
                       mol_type = other DNA
                       organism = synthetic construct
SEQUENCE: 278
cgtaatggtg ccgcgtatgt tg                                        22

SEQ ID NO: 279         moltype = DNA  length = 22
FEATURE                Location/Qualifiers
misc_feature           1..22
                       note = Description of Artificial Sequence: Syntheticprimer
source                 1..22
                       mol_type = other DNA
                       organism = synthetic construct
SEQUENCE: 279
cgtagaggtg cagaatacgt tg                                        22

SEQ ID NO: 280         moltype = DNA  length = 24
FEATURE                Location/Qualifiers
misc_feature           1..24
                       note = Description of Artificial Sequence: Syntheticprimer
source                 1..24
                       mol_type = other DNA
                       organism = synthetic construct
SEQUENCE: 280
ccaatatgga agacatcgta aacg                                      24

SEQ ID NO: 281         moltype = DNA  length = 21
FEATURE                Location/Qualifiers
misc_feature           1..21
                       note = Description of Artificial Sequence: Syntheticprimer
source                 1..21
                       mol_type = other DNA
                       organism = synthetic construct
SEQUENCE: 281
ccaattccgt atcggtttat c                                         21

SEQ ID NO: 282         moltype = DNA  length = 21
FEATURE                Location/Qualifiers
misc_feature           1..21
                       note = Description of Artificial Sequence: Syntheticprimer
source                 1..21
                       mol_type = other DNA
                       organism = synthetic construct
SEQUENCE: 282
ccaattccgt attggtttat c                                         21

SEQ ID NO: 283         moltype = DNA  length = 20
```

-continued

```
FEATURE                   Location/Qualifiers
misc_feature              1..20
                          note = Description of Artificial Sequence: Syntheticprimer
source                    1..20
                          mol_type = other DNA
                          organism = synthetic construct
SEQUENCE: 283
acttccattt gagcacgttc                                                20

SEQ ID NO: 284            moltype = DNA  length = 20
FEATURE                   Location/Qualifiers
misc_feature              1..20
                          note = Description of Artificial Sequence: Syntheticprimer
source                    1..20
                          mol_type = other DNA
                          organism = synthetic construct
SEQUENCE: 284
acttccattt gggcacgttc                                                20

SEQ ID NO: 285            moltype = DNA  length = 20
FEATURE                   Location/Qualifiers
misc_feature              1..20
                          note = Description of Artificial Sequence: Syntheticprimer
source                    1..20
                          mol_type = other DNA
                          organism = synthetic construct
SEQUENCE: 285
acttccattt gtgcacgttc                                                20

SEQ ID NO: 286            moltype = DNA  length = 21
FEATURE                   Location/Qualifiers
misc_feature              1..21
                          note = Description of Artificial Sequence: Syntheticprimer
source                    1..21
                          mol_type = other DNA
                          organism = synthetic construct
SEQUENCE: 286
gtgaacgtgc tcaaatggaa g                                              21

SEQ ID NO: 287            moltype = DNA  length = 21
FEATURE                   Location/Qualifiers
misc_feature              1..21
                          note = Description of Artificial Sequence: Syntheticprimer
source                    1..21
                          mol_type = other DNA
                          organism = synthetic construct
SEQUENCE: 287
gtgaacgtgc ccaaatggaa g                                              21

SEQ ID NO: 288            moltype = DNA  length = 21
FEATURE                   Location/Qualifiers
misc_feature              1..21
                          note = Description of Artificial Sequence: Syntheticprimer
source                    1..21
                          mol_type = other DNA
                          organism = synthetic construct
SEQUENCE: 288
gtgaacgtgc acaaatggaa g                                              21

SEQ ID NO: 289            moltype = DNA  length = 23
FEATURE                   Location/Qualifiers
misc_feature              1..23
                          note = Description of Artificial Sequence: Syntheticprimer
source                    1..23
                          mol_type = other DNA
                          organism = synthetic construct
SEQUENCE: 289
acatagctat cttcttcatc agc                                            23

SEQ ID NO: 290            moltype = DNA  length = 23
FEATURE                   Location/Qualifiers
misc_feature              1..23
                          note = Description of Artificial Sequence: Syntheticprimer
source                    1..23
                          mol_type = other DNA
                          organism = synthetic construct
SEQUENCE: 290
acgtaactat cctcttcatc agc                                            23
```

-continued

```
SEQ ID NO: 291          moltype = DNA   length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 291
acatagctat cctcttcatc agc                                         23

SEQ ID NO: 292          moltype = DNA   length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 292
acatagctat cttcttcgtc agc                                         23

SEQ ID NO: 293          moltype = DNA   length = 23
FEATURE                 Location/Qualifiers
misc_feature            1..23
                        note = Description of Artificial Sequence: Syntheticprimer
source                  1..23
                        mol_type = other DNA
                        organism = synthetic construct
SEQUENCE: 293
acataactgt cttcttcatc agc                                         23

SEQ ID NO: 294          moltype = DNA   length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 294
tcggtgagat ggaggtatgg                                             20

SEQ ID NO: 295          moltype = DNA   length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 295
tcggtgagat ggaagtatgg                                             20

SEQ ID NO: 296          moltype = DNA   length = 20
FEATURE                 Location/Qualifiers
misc_feature            1..20
                        note = Description of Artificial Sequence: Syntheticprimer
source                  1..20
                        mol_type = other DNA
                        organism = synthetic construct
SEQUENCE: 296
tcggtgaaat ggaagtatgg                                             20

SEQ ID NO: 297          moltype = DNA   length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 297
ctcggaatga ttctggaaca c                                           21

SEQ ID NO: 298          moltype = DNA   length = 21
FEATURE                 Location/Qualifiers
misc_feature            1..21
                        note = Description of Artificial Sequence: Syntheticprimer
source                  1..21
                        mol_type = other DNA
                        organism = synthetic construct
SEQUENCE: 298
ctcggaatga ttcaggaaca c                                           21
```

```
SEQ ID NO: 299          moltype = DNA   length = 18
FEATURE                 Location/Qualifiers
misc_feature            1..18
                        note = Description of Artificial Sequence: Syntheticprimer
source                  1..18
                        mol_type = other DNA
                        organism = synthetic construct
SEQUENCE: 299
gaagaagcag ttcggcaa                                                 18

SEQ ID NO: 300          moltype = DNA   length = 17
FEATURE                 Location/Qualifiers
misc_feature            1..17
                        note = Description of Artificial Sequence: Syntheticprimer
source                  1..17
                        mol_type = other DNA
                        organism = synthetic construct
SEQUENCE: 300
gagtcgatga cgatcat                                                  17

SEQ ID NO: 301          moltype = DNA   length = 18
FEATURE                 Location/Qualifiers
misc_feature            1..18
                        note = Description of Artificial Sequence: Syntheticprimer
source                  1..18
                        mol_type = other DNA
                        organism = synthetic construct
SEQUENCE: 301
ccacgctcac gctgcagg                                                 18

SEQ ID NO: 302          moltype = DNA   length = 18
FEATURE                 Location/Qualifiers
misc_feature            1..18
                        note = Description of Artificial Sequence: Syntheticprimer
source                  1..18
                        mol_type = other DNA
                        organism = synthetic construct
SEQUENCE: 302
cgagcccgag cgcaccag                                                 18

SEQ ID NO: 303          moltype = DNA   length = 17
FEATURE                 Location/Qualifiers
misc_feature            1..17
                        note = Description of Artificial Sequence: Syntheticprimer
source                  1..17
                        mol_type = other DNA
                        organism = synthetic construct
SEQUENCE: 303
cgaaggcgag atgggcg                                                  17

SEQ ID NO: 304          moltype = DNA   length = 16
FEATURE                 Location/Qualifiers
misc_feature            1..16
                        note = Description of Artificial Sequence: Syntheticprimer
source                  1..16
                        mol_type = other DNA
                        organism = synthetic construct
SEQUENCE: 304
tcgagacgca ccgacg                                                   16

SEQ ID NO: 305          moltype = DNA   length = 19
FEATURE                 Location/Qualifiers
misc_feature            1..19
                        note = Description of Artificial Sequence: Syntheticprimer
source                  1..19
                        mol_type = other DNA
                        organism = synthetic construct
SEQUENCE: 305
gtgcaggcga agatcgtcg                                                19

SEQ ID NO: 306          moltype = DNA   length = 17
FEATURE                 Location/Qualifiers
misc_feature            1..17
                        note = Description of Artificial Sequence: Syntheticprimer
source                  1..17
                        mol_type = other DNA
                        organism = synthetic construct
SEQUENCE: 306
```

```
ccatcgcctc ggcttcg                                                    17

SEQ ID NO: 307         moltype = DNA   length = 21
FEATURE                Location/Qualifiers
misc_feature           1..21
                       note = Description of Artificial Sequence: Syntheticprimer
source                 1..21
                       mol_type = other DNA
                       organism = synthetic construct
SEQUENCE: 307
ggcggacgtc acactccatt c                                               21

SEQ ID NO: 308         moltype = DNA   length = 24
FEATURE                Location/Qualifiers
misc_feature           1..24
                       note = Description of Artificial Sequence: Syntheticprimer
source                 1..24
                       mol_type = other DNA
                       organism = synthetic construct
SEQUENCE: 308
ccgtcttcga tagcgattgg gtgg                                            24

SEQ ID NO: 309         moltype = DNA   length = 23
FEATURE                Location/Qualifiers
misc_feature           1..23
                       note = Description of Artificial Sequence: Syntheticprimer
source                 1..23
                       mol_type = other DNA
                       organism = synthetic construct
SEQUENCE: 309
ggttgctcgt gaagacatcc aac                                             23

SEQ ID NO: 310         moltype = DNA   length = 23
FEATURE                Location/Qualifiers
misc_feature           1..23
                       note = Description of Artificial Sequence: Syntheticprimer
source                 1..23
                       mol_type = other DNA
                       organism = synthetic construct
SEQUENCE: 310
caccagtaac gtctgttgta cgg                                             23

SEQ ID NO: 311         moltype = DNA   length = 25
FEATURE                Location/Qualifiers
misc_feature           1..25
                       note = Description of Artificial Sequence: Syntheticprimer
source                 1..25
                       mol_type = other DNA
                       organism = synthetic construct
SEQUENCE: 311
caggcgatga tgttccagtt atcgc                                           25

SEQ ID NO: 312         moltype = DNA   length = 24
FEATURE                Location/Qualifiers
misc_feature           1..24
                       note = Description of Artificial Sequence: Syntheticprimer
source                 1..24
                       mol_type = other DNA
                       organism = synthetic construct
SEQUENCE: 312
gtagcaacag taccacgtcc agtg                                            24

SEQ ID NO: 313         moltype = DNA   length = 38
FEATURE                Location/Qualifiers
misc_feature           1..38
                       note = Description of Artificial Sequence: Syntheticprimer
source                 1..38
                       mol_type = other DNA
                       organism = synthetic construct
SEQUENCE: 313
tgtaaaacga cggccagtgc nggrtcytty tcytgrca                             38

SEQ ID NO: 314         moltype = DNA   length = 18
FEATURE                Location/Qualifiers
misc_feature           1..18
                       note = Description of Artificial Sequence: Syntheticprimer
source                 1..18
                       mol_type = other DNA
                       organism = synthetic construct
```

-continued

```
SEQUENCE: 314
tgtaaaacga cggccagt                                              18

SEQ ID NO: 315        moltype = DNA  length = 37
FEATURE               Location/Qualifiers
misc_feature          1..37
                      note = Description of Artificial Sequence: Syntheticprimer
source                1..37
                      mol_type = other DNA
                      organism = synthetic construct
SEQUENCE: 315
caggaaacag ctatgaccay gsnggnggna arttyra                         37

SEQ ID NO: 316        moltype = DNA  length = 18
FEATURE               Location/Qualifiers
misc_feature          1..18
                      note = Description of Artificial Sequence: Syntheticprimer
source                1..18
                      mol_type = other DNA
                      organism = synthetic construct
SEQUENCE: 316
caggaaacag ctatgacc                                              18

SEQ ID NO: 317        moltype = DNA  length = 19
FEATURE               Location/Qualifiers
misc_feature          1..19
                      note = Description of Artificial Sequence: Syntheticprimer
source                1..19
                      mol_type = other DNA
                      organism = synthetic construct
SEQUENCE: 317
cagctgggac atcctggcc                                             19

SEQ ID NO: 318        moltype = DNA  length = 24
FEATURE               Location/Qualifiers
misc_feature          1..24
                      note = Description of Artificial Sequence: Syntheticprimer
source                1..24
                      mol_type = other DNA
                      organism = synthetic construct
SEQUENCE: 318
tgagggatgt tgttggtaaa gcac                                       24

SEQ ID NO: 319        moltype = DNA  length = 24
FEATURE               Location/Qualifiers
misc_feature          1..24
                      note = Description of Artificial Sequence: Syntheticprimer
source                1..24
                      mol_type = other DNA
                      organism = synthetic construct
SEQUENCE: 319
gtgctttacc aacaacatcc ctca                                       24

SEQ ID NO: 320        moltype = DNA  length = 23
FEATURE               Location/Qualifiers
misc_feature          1..23
                      note = Description of Artificial Sequence: Syntheticprimer
source                1..23
                      mol_type = other DNA
                      organism = synthetic construct
SEQUENCE: 320
tgtctttggt ctgggagctg aac                                        23

SEQ ID NO: 321        moltype = DNA  length = 60
FEATURE               Location/Qualifiers
misc_feature          1..60
                      note = Description of Artificial Sequence: Syntheticprimer
modified_base         48
                      mod_base = i
source                1..60
                      mol_type = other DNA
                      organism = synthetic construct
SEQUENCE: 321
ccatctcatc cctgcgtgtc tccgactcag acgctcgaca agyggcgnac gggtgagtaa  60

SEQ ID NO: 322        moltype = DNA  length = 60
FEATURE               Location/Qualifiers
misc_feature          1..60
                      note = Description of Artificial Sequence: Syntheticprimer
```

-continued

```
modified_base          48
                       mod_base = i
source                 1..60
                       mol_type = other DNA
                       organism = synthetic construct
SEQUENCE: 322
ccatctcatc cctgcgtgtc tccgactcag agacgcactc agyggcgnac gggtgagtaa  60

SEQ ID NO: 323         moltype = DNA  length = 60
FEATURE                Location/Qualifiers
misc_feature           1..60
                       note = Description of Artificial Sequence: Syntheticprimer
modified_base          48
                       mod_base = i
source                 1..60
                       mol_type = other DNA
                       organism = synthetic construct
SEQUENCE: 323
ccatctcatc cctgcgtgtc tccgactcag agcactgtag agyggcgnac gggtgagtaa  60

SEQ ID NO: 324         moltype = DNA  length = 60
FEATURE                Location/Qualifiers
misc_feature           1..60
                       note = Description of Artificial Sequence: Syntheticprimer
modified_base          48
                       mod_base = i
source                 1..60
                       mol_type = other DNA
                       organism = synthetic construct
SEQUENCE: 324
ccatctcatc cctgcgtgtc tccgactcag atcagacacg agyggcgnac gggtgagtaa  60

SEQ ID NO: 325         moltype = DNA  length = 60
FEATURE                Location/Qualifiers
misc_feature           1..60
                       note = Description of Artificial Sequence: Syntheticprimer
modified_base          48
                       mod_base = i
source                 1..60
                       mol_type = other DNA
                       organism = synthetic construct
SEQUENCE: 325
ccatctcatc cctgcgtgtc tccgactcag atatcgcgag agyggcgnac gggtgagtaa  60

SEQ ID NO: 326         moltype = DNA  length = 60
FEATURE                Location/Qualifiers
misc_feature           1..60
                       note = Description of Artificial Sequence: Syntheticprimer
modified_base          48
                       mod_base = i
source                 1..60
                       mol_type = other DNA
                       organism = synthetic construct
SEQUENCE: 326
ccatctcatc cctgcgtgtc tccgactcag cgtgtctcta agyggcgnac gggtgagtaa  60

SEQ ID NO: 327         moltype = DNA  length = 60
FEATURE                Location/Qualifiers
misc_feature           1..60
                       note = Description of Artificial Sequence: Syntheticprimer
modified_base          48
                       mod_base = i
source                 1..60
                       mol_type = other DNA
                       organism = synthetic construct
SEQUENCE: 327
ccatctcatc cctgcgtgtc tccgactcag ctcgcgtgtc agyggcgnac gggtgagtaa  60

SEQ ID NO: 328         moltype = DNA  length = 60
FEATURE                Location/Qualifiers
misc_feature           1..60
                       note = Description of Artificial Sequence: Syntheticprimer
source                 1..60
                       mol_type = other DNA
                       organism = synthetic construct
SEQUENCE: 328
ccatctcatc cctgcgtgtc tccgactcag acgctcgaca actcctacgg gaggcagcag  60

SEQ ID NO: 329         moltype = DNA  length = 60
```

```
FEATURE                 Location/Qualifiers
misc_feature            1..60
                        note = Description of Artificial Sequence: Syntheticprimer
source                  1..60
                        mol_type = other DNA
                        organism = synthetic construct
SEQUENCE: 329
ccatctcatc cctgcgtgtc tccgactcag agacgcactc actcctacgg gaggcagcag  60

SEQ ID NO: 330          moltype = DNA  length = 60
FEATURE                 Location/Qualifiers
misc_feature            1..60
                        note = Description of Artificial Sequence: Syntheticprimer
source                  1..60
                        mol_type = other DNA
                        organism = synthetic construct
SEQUENCE: 330
ccatctcatc cctgcgtgtc tccgactcag agcactgtag actcctacgg gaggcagcag  60

SEQ ID NO: 331          moltype = DNA  length = 60
FEATURE                 Location/Qualifiers
misc_feature            1..60
                        note = Description of Artificial Sequence: Syntheticprimer
source                  1..60
                        mol_type = other DNA
                        organism = synthetic construct
SEQUENCE: 331
ccatctcatc cctgcgtgtc tccgactcag atcagacacg actcctacgg gaggcagcag  60

SEQ ID NO: 332          moltype = DNA  length = 60
FEATURE                 Location/Qualifiers
misc_feature            1..60
                        note = Description of Artificial Sequence: Syntheticprimer
source                  1..60
                        mol_type = other DNA
                        organism = synthetic construct
SEQUENCE: 332
ccatctcatc cctgcgtgtc tccgactcag atatcgcgag actcctacgg gaggcagcag  60

SEQ ID NO: 333          moltype = DNA  length = 60
FEATURE                 Location/Qualifiers
misc_feature            1..60
                        note = Description of Artificial Sequence: Syntheticprimer
source                  1..60
                        mol_type = other DNA
                        organism = synthetic construct
SEQUENCE: 333
ccatctcatc cctgcgtgtc tccgactcag cgtgtctcta actcctacgg gaggcagcag  60

SEQ ID NO: 334          moltype = DNA  length = 60
FEATURE                 Location/Qualifiers
misc_feature            1..60
                        note = Description of Artificial Sequence: Syntheticprimer
source                  1..60
                        mol_type = other DNA
                        organism = synthetic construct
SEQUENCE: 334
ccatctcatc cctgcgtgtc tccgactcag acgagtgcgt actcctacgg gaggcagcag  60

SEQ ID NO: 335          moltype = DNA  length = 47
FEATURE                 Location/Qualifiers
misc_feature            1..47
                        note = Description of Artificial Sequence: Syntheticprimer
source                  1..47
                        mol_type = other DNA
                        organism = synthetic construct
SEQUENCE: 335
acactgacga catggttcta caaaactcgg tcatttagag gaagtaa              47

SEQ ID NO: 336          moltype = DNA  length = 41
FEATURE                 Location/Qualifiers
misc_feature            1..41
                        note = Description of Artificial Sequence: Syntheticprimer
source                  1..41
                        mol_type = other DNA
                        organism = synthetic construct
SEQUENCE: 336
tacggtagca gagacttggt ctgctgcgtt cttcatcgat g                    41
```

-continued

```
SEQ ID NO: 337         moltype = DNA  length = 42
FEATURE                Location/Qualifiers
misc_feature           1..42
                       note = Description of Artificial Sequence: Syntheticprimer
source                 1..42
                       mol_type = other DNA
                       organism = synthetic construct
SEQUENCE: 337
acactgacga catggttcta caatcgagtc tttgaacgca ca                      42

SEQ ID NO: 338         moltype = DNA  length = 42
FEATURE                Location/Qualifiers
misc_feature           1..42
                       note = Description of Artificial Sequence: Syntheticprimer
source                 1..42
                       mol_type = other DNA
                       organism = synthetic construct
SEQUENCE: 338
tacggtagca gagacttggt ctcctacctg atccgaggtc aa                      42
```